United States Patent [19]
Champness et al.

[11] Patent Number: 5,876,987
[45] Date of Patent: Mar. 2, 1999

[54] METHOD, DNA AND BACTERIA FOR HYPERPRODUCTION OF AN ANTIBIOTIC DUE TO DISRUPTION OF AN ABSA GENE

[75] Inventors: Wendy C. Champness, East Lansing, Mich.; Paul Brian, San Diego, Calif.; Todd B. Anderson, East Lansing, Mich.

[73] Assignee: Board of Trustees operating Michigan State University, East Lansing, Mich.

[21] Appl. No.: 796,414

[22] Filed: Feb. 6, 1997

Related U.S. Application Data

[60] Provisional application No. 60/011,286 Feb. 7, 1996.
[51] Int. Cl.[6] .......................... C12N 15/10; C12N 1/21; C07H 21/04
[52] U.S. Cl. .................. 435/172.3; 435/252.35; 536/23.2; 536/23.7
[58] Field of Search .......................... 435/252.3, 252.35, 435/253.5, 172.3, 172.1, 320.1; 536/23.1, 23.7, 23.2

[56] References Cited

U.S. PATENT DOCUMENTS

| | | | |
|---|---|---|---|
| 4,362,816 | 12/1982 | Reusser | 435/91.41 |
| 4,898,828 | 2/1990 | Hershberger et al. | 435/252.3 |
| 5,118,617 | 6/1992 | Ortega et al. | 435/69.1 |
| 5,122,595 | 6/1992 | Ortega et al. | 530/350 |
| 5,264,354 | 11/1993 | Solenberg | 435/172.3 |
| 5,435,730 | 7/1995 | Adams | 435/69.1 |
| 5,474,912 | 12/1995 | Sherman et al. | 435/43 |

OTHER PUBLICATIONS

Fernandez–Moreno, M.A., et al., Cell 66:769–780 (1991).
Gramajo, H.C., et al., Mol. Microbiol. 7:837–845 (1993).
Champness, W.C., J. Bacteriol. 170:1168–1174 (1988).
Fernandez–Moreno, M.A., et al., J. Bacteriol. 174:2958–2967 (1992).
Ishizuka, H., et al., J. Bacteriol. 174:7585–7594 (1992).
Stein, D., et al., J. Bacteriol. 171:2258–2261 (1989).
Adamidis, T., et al., J. Bacteriol. 172:2962–2969 (1990).
Adamidis, T., et al., J. Bacteiriol. 174:4622–4628 (1992).
Janssen, G.R., et al., Gene 124:133–134 (1993).
Bruton, C., et al., Bio/Technology 9:652–656 (1991).
Bibb, M. J., et al., Gene 41:357–368 (1986).
Guthrie, E.P., et al., J. Bacteriol. 172:6189–6193 (1990).
Parkinson, J.S., et al., Ann. Rev. Genet. 26:71–112 (1992).
Brian, P., et al., J. of Bacteriology, pp. 3221–3231 (1996).
Dahl, M.K., et al., J. Biol. Chem. 267:14509–14514 (1992).
Matsumoto, A., et al., Gene 146:47–56 (1994).
Champness, W.C., et al., Gene 115:55–60 (1992).
Laville, J., et al., Proc. Natl. Acad. Sci. 89:1562–1566 (1992).
Corbell, N., et al., J. Bacteiriol. 177:6230–6236 (1995).
Otten, S.L., et al., J. Bacteriol. 177:1216–1224 (1995).
Bainton, N.J., et al., Gene 116:87–91 (1992).
McGowan, S., et al., Microbiology 141:541–550 (1995).
Chater, K.F., Bio/Technology 8:115–121 (1990).

*Primary Examiner*—David Guzo
*Attorney, Agent, or Firm*—Ian C. McLeod

[57] ABSTRACT

A recombinant *Streptomyces sp.* which exhibits hyperproduction of an antibiotic, particularly actinorhodin and undecylprodigiosin, as a result of interruption of the absA homologous locus of chromosomal DNA (SEQ ID NO:1) is described. The gene is thought to encode a histidine kinase and a response regulator. The preferred bacterium is *Streptomyces coelicolor*. It is preferred to interrupt the absA1 gene with ermE DNA.

20 Claims, 12 Drawing Sheets

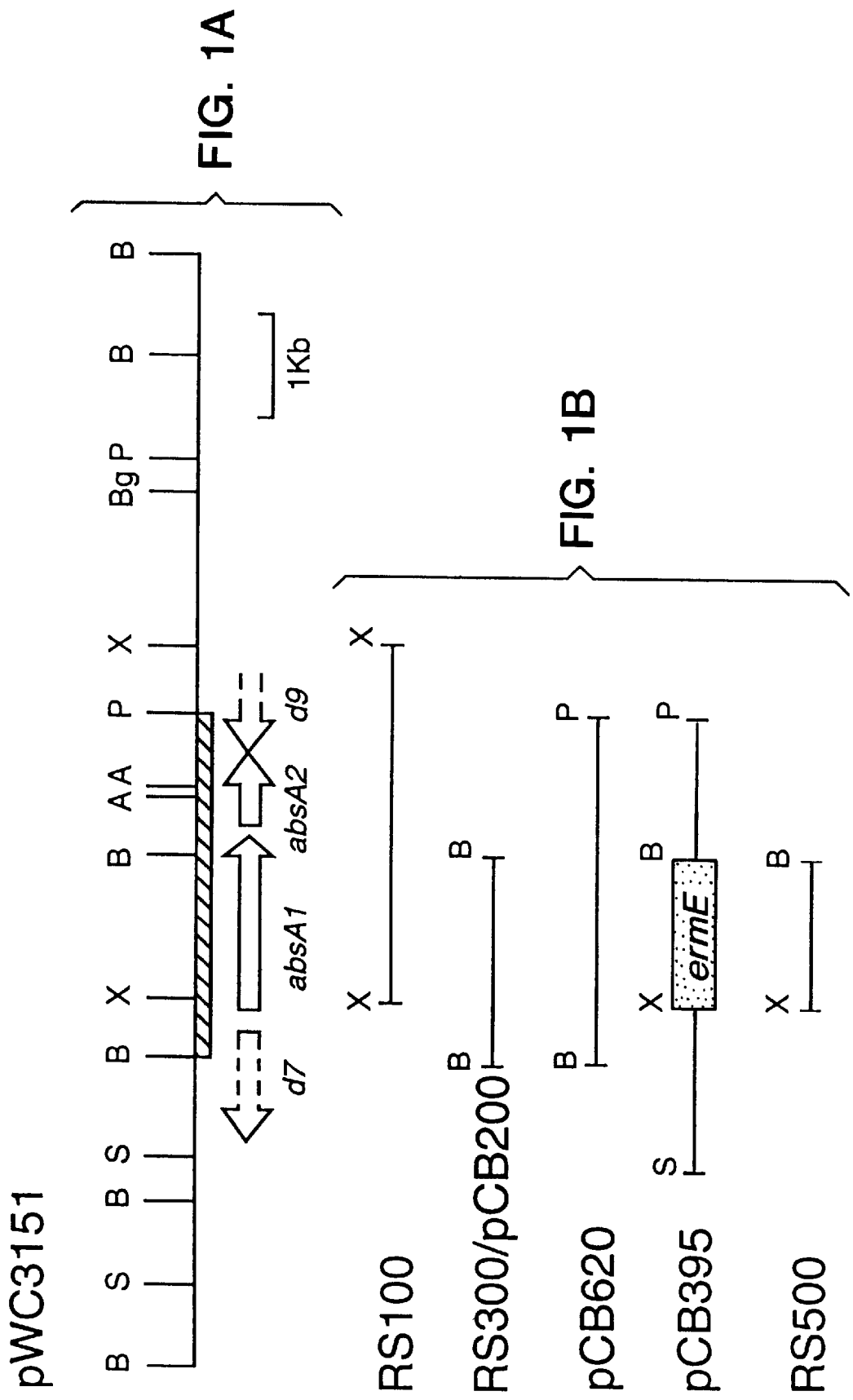

```
      I  G  N  S  R  A  L  G  L  P  H  H  R  A  S  R  G  P  H
  1 ---------+---------+---------+---------+---------+---------+  60
    CCTAGGGCAACGACGCCCGGTCGGGCTCGCCCACCACGGCCCGGCTTGCCGGCCCCACCG
    BamHI

G  A  R  A  D  L  L  A  G  V  E  R  L  P  H  R  L  E  E  Y
 61 ---------+---------+---------+---------+---------+---------+ 120
    GGCGCGCCCGCAGCTCGTCGCGTGGCTGGAGCGCGTTGCCCACGGCGTCGAGGAGCATTG

R  K  G  G  V  L  A  R  G  S  T  P  A  D  L  G  V  I  M  R
121 ---------+---------+---------+---------+---------+---------+ 180
    CGAACGGCGGGTGGTCCCGGGCGGGGCTCCACCCGCGCAGGTCTGGCTGCTAGTACGCGT

M  T  T  S  K  G  A  G  N  P  G  L  F  G  T  V  K  G  P  N
181 ---------+---------+---------+---------+---------+---------+ 240
    AGCAGCAGCTGAAAGGGCGCGGCAAGCCCGGCTCCTTAGGCCACTGGAAAGGGCCTAACT

I  E  F  S  L  D  S  V  A  T  K  D  G  Y  R  K  T  L  R  D
241 ---------+---------+---------+---------+---------+---------+ 300
    AGAGCTTGCTCTCCAGGCTCTGCCGGCAGAACAGCGGCATGGCGAACCAGTCAGCCAGGT

L  T  I  M
    Start of D7       GCCTGGTGGCTCCTTCCAAAGTCACGTCCTCAACGCTAGGGAGAGGCAG
301 ---------+---------+---------+---------+---------+---------+ 360
    TTCACTAGTAGCGGACCACCGAGGAAGGTTTCAGTGCAGGAGTTGCGATCCCTCTCCGTC GGGCACGAAACATCTGGCGATCGGCAACGACCGCAGTCGACTTTCGGCAGATCCGGCGGC
361 ---------+---------+---------+---------+---------+---------+ 420
    CCCGTGCTTTGTAGACCGCTAGCCGTTGCTGGCGTCAGCTGAAAGCCGTCTAGGCCGCCG CGGGGCCGCTCTTGTAGCGTGCTGGAATGCACCGATGGCAGGCCGTGCGCCGACGAATCG
421 ---------+---------+---------+---------+---------+---------+ 480
    GCCCCGGCGAGAACATCGCACGACCT    Start of AbsA1
                              M  H  R  W  Q  A  V  R  R  R  I  E AATCGCTTGTACGGGTCCTCGGCTCCGAGCGCCCGTTCACCCGGCGCGCCGATCTGGTGC
481 ---------+---------+---------+---------+---------+---------+ 540
        S  L  V  R  V  L  G  S  E  R  P  F  T  R  R  A  D  L  V  L
                                                   XhoI
    TGCTGCTCGTACTGCTCGTGCCCTCCGCGTTCGCCACCGGGACGCTCGAGACCGCGCCGG
541 ---------+---------+---------+---------+---------+---------+ 600
        L  L  V  L  L  V  P  S  A  F  A  T  G  T  L  E  T  A  P  V TCGCCTGGCTGACCGCGTGTCTGCTCATCGCGGCCGCGGTCGTGGTGCAGCGCACCGCGC
601 ---------+---------+---------+---------+---------+---------+ 660
        A  W  L  T  A  C  L  L  I  A  A  A  V  V  V  Q  R  T  A  P CGCTGCTGTCCCTGCTGCTCGCGGCGCTGCTCACGCTGTTCTATCCGTGGTTCGGGGCGA
661 ---------+---------+---------+---------+---------+---------+ 720
        L  L  S  L  L  L  A  A  L  L  T  L  F  Y  P  W  F  G  A  N ACCTGTGGCCGTCGATGGCGACGGTGGTGCTGAGCTGCCTCGCGGGCCGCAGACTGACCC
721 ---------+---------+---------+---------+---------+---------+ 780
        L  W  P  S  M  A  T  V  V  L  S  C  L  A  G  R  R  L  T  R
```

FIG. 4A

```
                GGCTGTGGCCCGCGCACCTGGTGTTCCTCTGTGTCGCCGCGGCCGGGCTCCTGCTGGTGG
    781      ----------+---------+---------+---------+---------+---------+   840
                 L  W  P  A  H  L  V  F  L  C  V  A  A  A  G  L  L  L  V  A

CCACCGTCGGCCAGGGCAAGGACTGGCTGAGCCTGCTGATGACCGAGTTCGTCGCCTGTG
    841      ----------+---------+---------+---------+---------+---------+   900
                 T  V  G  Q  G  K  D  W  L  S  L  L  M  T  E  F  V  A  C  V
                                                                       NaeI
                TGCTGCCCTGGTGGGCGGGCAACTGGTGGAGCCAGCGCACCGCGCTGACCCACGCCGGCT
    901      ----------+---------+---------+---------+---------+---------+   960
                 L  P  W  W  A  G  N  W  W  S  Q  R  T  A  L  T  H  A  G  W

GGGAGCACGCCGAGCAACTGGAGTGGCGCCAGCGCTACATCGCCGACCAGGCCAGGATGA
    961      ----------+---------+---------+---------+---------+---------+  1020
                 E  H  A  E  Q  L  E  W  R  Q  R  Y  I  A  D  Q  A  R  M  K

AGGAGCGGGCCAGGATCGCGCAGGACATCCACGACTCCCTGGGCCACGAACTGAGCGTGA
   1021      ----------+---------+---------+---------+---------+---------+  1080
                 E  R  A  R  I  A  Q  D  I  H  D  S  L  G  H  E  L  S  V  M

TGGCCCTGCTCGCCGGCGGCCTGGAGCTGGCCCCCGGGCTGTCGGACCCGCACCGGGAGT
   1081      ----------+---------+---------+---------+---------+---------+  1140
                 A  L  L  A  G  G  L  E  L  A  P  G  L  S  D  P  H  R  E  S

CGGTGGGCCAGTTGCGGGAGCGGTGCACGATGGCCACCGAGCGGCTGCACGAGGTGATCG
   1141      ----------+---------+---------+---------+---------+---------+  1200
                 V  G  Q  L  R  E  R  C  T  M  A  T  E  R  L  H  E  V  I  G

GGCTGCTGCGGGAGGACCCCAATCCGTCGCTGACCCCCGCCGACGAGTCCGTCGCCCAGC
   1201      ----------+---------+---------+---------+---------+---------+  1260
                 L  L  R  E  D  P  N  P  S  L  T  P  A  D  E  S  V  A  Q  L

TCGTGCGCCGTTTCCAGCGCTCCGGTACGCCGGTCCGGTTCCAGGAGGACGGGGCCCGGG
   1261      ----------+---------+---------+---------+---------+---------+  1320
                 V  R  R  F  Q  R  S  G  T  P  V  R  F  Q  E  D  G  A  R  D

ACCGCCCCGGCACGCCGCTGCTGTCCGACCTCGCGGCCTACCGGGTGGTGCAGGAGGCGC
   1321      ----------+---------+---------+---------+---------+---------+  1380
                 R  P  G  T  P  L  L  S  D  L  A  A  Y  R  V  V  Q  E  A  L

TGACGAACGCGGCCAAGCACGCGCCGGGCGCGCCCATCGACGTACGGGTGACGCACACCG
   1381      ----------+---------+---------+---------+---------+---------+  1440
                 T  N  A  A  K  H  A  P  G  A  P  I  D  V  R  V  T  H  T  A

CGGACGAGACGGTGGTGTCGGTCGTCAACGAGCGGCCGGAGCGGGGCGGGAGTGTTCCGG
   1441      ----------+---------+---------+---------+---------+---------+  1500
                 D  E  T  V  V  S  V  V  N  E  R  P  E  R  G  G  S  V  P  A

CGGCCGGGAGCGGGTCGGGGCTGATCGGCCTCGACGAGCGGGTCCGGCTCGCGGGCGGCA
   1501      ----------+---------+---------+---------+---------+---------+  1560
                 A  G  S  G  S  G  L  I  G  L  D  E  R  V  R  L  A  G  G  T

CGCTGCGCACGGGCCCGCGGGCGGGCGGTTTCGAGGTGTACGCGCGACTGCCGCGCGGCG
   1561      ----------+---------+---------+---------+---------+---------+  1620
                 L  R  T  G  P  R  A  G  G  F  E  V  Y  A  R  L  P  R  G  A

CCTCCTCGCCGTCGCGGTCCACCGAGCCGCCGGGGCCGGCCGACGGGGACGGCACGGCCG
   1621      ----------+---------+---------+---------+---------+---------+  1680
                 S  S  P  S  R  S  T  E  P  P  G  P  A  D  G  D  G  T  A  G
```

FIG. 4B

```
                                                            NaeI
          GTGGCTCGGGCGACGGCACGGCGCCCGGGGCCGCGACGGCCGGCAACGAGGGGCGGGCCG
     1681 ---------+---------+---------+---------+---------+---------+ 1740
            G  S  G  D  G  T  A  P  G  A  A  T  A  G  N  E  G  R  A  A

CGGCCGCCGCGGCGGACCTGCCCGCCCCCTCCGGGCCGTGGCGCAGCGCCTCCCGGGCCG
     1741 ---------+---------+---------+---------+---------+---------+ 1800
            A  A  A  A  D  L  P  A  P  S  G  P  W  R  S  A  S  R  A  A

CGCTGCTGCGCACCCGGGCCCGGATCAGGCGGGACGCCCGGCGGGCCGCGCTGATACCGG
     1801 ---------+---------+---------+---------+---------+---------+ 1860
            L  L  R  T  R  A  R  I  R  R  D  A  R  R  A  A  L  I  P  A

CGGTGCTCGGCGCCGCCATCGTGGCCTTCCTCGGCGGGCTCTACGTCTTCACCTCGGCGA
     1861 ---------+---------+---------+---------+---------+---------+ 1920
            V  L  G  A  A  I  V  A  F  L  G  G  L  Y  V  F  T  S  A  T
                                           BamHI
          CCACGTCCCTCGCCCCCGAGGACTACGCCCGGATCCGGGTGGGCGAGACCCGCGCCGATC
     1921 ---------+---------+---------+---------+---------+---------+ 1980
            T  S  L  A  P  E  D  Y  A  R  I  R  V  G  E  T  R  A  D  L

TGGCCCCCGCGCTGCCGGAGCGCCGGATCAAGAAGCCGCCGCCGGTCACCTCCGAGCCGT
     1981 ---------+---------+---------+---------+---------+---------+ 2040
            A  P  A  L  P  E  R  R  I  K  K  P  P  P  V  T  S  E  P  S

CCGTCCCGGCCGGCACGACCTGCGAGTACTACCGGGCGAGCAGCGGTCTGCTCGACTTCG
     2041 ---------+---------+---------+---------+---------+---------+ 2100
            V  P  A  G  T  T  C  E  Y  Y  R  A  S  S  G  L  L  D  F  G

GCGGCGCCATGTACCGGCTGTGCTTCAAGGATGATGTCCTCATGGCCAAGGACACGCTCT
     2101 ---------+---------+---------+---------+---------+---------+ 2160
            G  A  M  Y  R  L  C  F  K  D  D  V  L  M  A  K  D  T  L  *
                                                              End of AbsA1
          GACCACCAGGGAAGGATCGGATGATTCGCGTACTGCTCGCCGACGACGAGACCATCATCA
     2161 ---------+---------+---------+---------+---------+---------+ 2220
                                  M  I  R  V  L  L  A  D  D  E  T  I  I  R
                               Start of AbsA2
          GGGCCGGGGTTCGCTCCATCCTGACGACCGAACCGGGCATCGAGGTGGTCGCCGAGGCGT
     2221 ---------+---------+---------+---------+---------+---------+ 2280
            A  G  V  R  S  I  L  T  T  E  P  G  I  E  V  V  A  E  A  S CCGACGGGCGGGAGGCGGTGGAACTGGCCCGCAAGCACCGGCCCGACGTGGCCCTGCTCG
     2281 ---------+---------+---------+---------+---------+---------+ 2340
            D  G  R  E  A  V  E  L  A  R  K  H  R  P  D  V  A  L  L  D ACATCCGGATGCCGGAGATGGACGGCCTGACGGCCGCGGGTGAGATGCGGACCACCAACC
     2341 ---------+---------+---------+---------+---------+---------+ 2400
            I  R  M  P  E  M  D  G  L  T  A  A  G  E  M  R  T  T  N  P
                                                                     ApaI
          CGGACACCGCGGTCGTCGTCCTCACCACCTTCGGGGAGGACCGGTACATCGAACGGGCCC
     2401 ---------+---------+---------+---------+---------+---------+ 2460
            D  T  A  V  V  V  L  T  T  F  G  E  D  R  Y  I  E  R  A  L TGGACCAGGGCGTGGCCGGGTTCCTGCTCAAGGCGTCCGATCCGCGGGACCTGATCTCCG
     2461 ---------+---------+---------+---------+---------+---------+ 2520
            D  Q  G  V  A  G  F  L  L  K  A  S  D  P  R  D  L  I  S  G
```

FIG. 4C

```
              GCGTACGGGCCGTGGCGTCCGGCGGCTCCTGCCTCTCCCCGCTGGTGGCGCGGCGGCTGA
2521   ---------+---------+---------+---------+---------+---------+ 2580
         V   R   A   V   A   S   G   G   S   C   L   S   P   L   V   A   R   R   L   M
                        ApaI
              TGACCGAGCTGCGCCGGGCCCCCTCACCGCGCTCGGAGGTGTCGGGGGAGCGCACGACGC
2581   ---------+---------+---------+---------+---------+---------+ 2640
           T   E   L   R   R   A   P   S   P   R   S   E   V   S   G   E   R   T   T   L

TGCTGACCAAGCGGGAGCAGGAGGTCCTCGGCATGCTGGGGGCCGGGCTGTCGAACGCGG
2641   ---------+---------+---------+---------+---------+---------+ 2700
           L   T   K   R   E   Q   E   V   L   G   M   L   G   A   G   L   S   N   A   E

AGATCGCGCAGCGGCTGCACCTGGTCGAGGGCACGATCAAGACGTATGTCAGCGCCATCT
2701   ---------+---------+---------+---------+---------+---------+ 2760
           I   A   Q   R   L   H   L   V   E   G   T   I   K   T   Y   V   S   A   I   F

TCACCCAGTTGGAGGTCCGCAACCGGGTGCAGGCGGCGATCATCGCGTACGAGGCGGGAC
2761   ---------+---------+---------+---------+---------+---------+ 2820
           T   Q   L   E   V   R   N   R   V   Q   A   A   I   I   A   Y   E   A   G   L

*   V   G   R   P   G   Q   R   L   P   G
              TGGTGAAGGACGCCGACCTCAACCGTTAG       End of D9
2821   ---------+---------+---------+---------+---------+---------+ 2880
                End of AbsA2       AATCTGCGGCGCGCCAGGAACTGCTTCGCCCGGTC
           V   K   D   A   D   L   N   R   *

A   A   D   G   G   R   R   R   P   R   H   H   P   L   Q   V   L   P   P   D
2881   ---------+---------+---------+---------+---------+---------+ 2940
              GGCGCAGCGGGGGAGCCGCCGCGCCAGCCACCACTCCATCGACGTGCTCTCCGCCTAGAC

A   P   R   G   R   R   G   P   P   L   P   A   D   P   D   L   H   R   R   V
2941   ---------+---------+---------+---------+---------+---------+ 3000
              GGCCAGCGGGCGCAGCAGGTCCACCTTCACCGCGTAGCCCCAGGTCTACTGCGGCATGAA

E   G   R   L   R   G   A   R   G   R   G   G   R   L   A   R   R   P   D   P
3001   ---------+---------+---------+---------+---------+---------+ 3060
              GAGGCGCCTCTGCAGGTCGCGCCGGAGCAGGCGGAGCTTCCCGTGCAGCTCCCAGTCCTT

L   V   R   R   G   P   R   E   V   A   R   R   G   I   G   T   R   R   A   A
3061   ---------+---------+---------+---------+---------+---------+ 3120
              CTTGGGCGGCAGGCCCAGCAAGGTGGCGTGCGGCGGGCTAAGGCCACGCGGCCCGCCGTC

T   R   R   R   P   H   R   A   P   V   A   D   H   V   P   L   P   P   G   L
3121   ---------+---------+---------+---------+---------+---------+ 3180
              AAGCCGCCGCTCCCACAGCGCGTCCGTGGCGTAGCACCTGACCATCACCGCCCGGCTCCG

G   R   E   G   G   A   T   G   R   R   E   A
3181   ---------+---------+---------+------ 3216
              GAGCAAGCGGCGGGCGTCAGGGGCGGCAAGACGTC
                                             PstI
```

FIG. 4D

METHOD, DNA AND BACTERIA FOR HYPERPRODUCTION OF AN ANTIBIOTIC DUE TO DISRUPTION OF AN ABSA GENE

GOVERNMENT RIGHTS

The present invention was supported by grants DMB8811338, MCB9206068 and a Career Advancement Award from the National Science Foundation, as well as grant BIR9120006 from the National Science Foundation. The Government has certain rights to this invention.

This application claims the benefit of U.S. Provisional Application No. 60/011,286 filing date Feb. 7, 1996.

BACKGROUND OF THE INVENTION

(1) Summary of the Invention

The present invention relates to the disruption of an AbsA gene in a bacterium, particularly a *Streptomyces sp.* so that there is hyperproduction of an antibiotic naturally produced by the bacterium. Streptomycete antibiotic synthesis in the wild type strain is coupled to morphological differentiation such that antibiotics are produced as a colony sporulates in the wild type strain. *Streptomyces coelicolor* produces several structurally and genetically distinct antibiotics. It has been found that the *S. coelicolor* absA locus was defined by UV-induced mutations that globally blocked antibiotic biosynthesis without blocking morphological differentiation. The present invention shows that the absA locus encodes a eubacterial two component sensor-kinase/response regulator system. All four UV mutations lie within a single open reading frame, designated absA1, which codes for the sensor-histidine kinase. A second gene downstream of absA1, absA2, encodes the cognate response regulator. In marked contrast to the antibiotic deficient phenotype of the previously described UV absA mutants, disruption mutations in the absA locus unexpectedly cause premature transcription of the biosynthetic genes for the antibiotics actinorhodin and undecylprodigiosin and precocious hyperproduction of both of these antibiotics. Thus the absA locus encodes a signal transduction mechanism that negatively regulates synthesis of the multiple antibiotics produced by *S. coelicolor*. This is also true of related *Streptomyces sp.*

(2) Description of Related Art

U.S. Pat. No. 4,362,816 to Reusser, U.S. Pat. No. 4,898,828 to Hershberger et al, U.S. Pat. No. 5,118,617 to Ortega et al, U.S. Pat. No. 5,122,595 to Ortega et al, U.S. Pat. No. 5,264,354 to Solenberq, U.S. Pat. No. 5,435,730 to Adams et al, and U.S. Pat. No. 5,474,912 to Sherman et al are of general interest. They describe various related species of Streptomyces.

The widespread use of chemotherapeutic agents has probably been the most significant advance in medicine in this century. The vast variety of compounds available for human health care is due in large part to the biosynthetic versatility of the streptomycetes. These bacteria have provided many thousands of structurally diverse, low molecular weight chemicals that are currently being exploited in both medicine and agriculture. Many streptomycete secondary metabolites have found commercial applications. Some of these are antibacterial drugs, including streptomycin and tetracycline; antiparasitic drugs such as avermectin; fungicidal agents such as polyoxin; antitumor drugs such as adriamycin and immunosuppressive drugs such as rapamycin. The biosynthetic pathways that produce these compounds have received considerable attention over the last few decades.

Advances in understanding the regulation of antibiotic synthesis in Streptomyces have come from the study of antibiotic synthesis in the genetically well characterized strain *Streptomyces coelicolor*. The four antibiotics produced by *S. coelicolor*, actinorhodin (Act), undecylprodigiosin (Red), calcium dependent antibiotic (CDA) and methylenomycin (Mmy), are biosynthetically and genetically distinct, genes for the synthesis of each of the antibiotics being encoded in genetically unlinked clusters. All four biosynthetic loci have been genetically well characterized and three biosynthetic gene clusters have been cloned; the act genes; the red genes; and the muny genes. Expression of act biosynthetic genes has been shown to depend on a gene, linked to the biosynthetic genes, designated actII-ORF4 (Fernandez-Moreno, M. A., et al., Cell 66:769–780 (1991); Gramajo, H. C., et al., Mol. Microbiol. 7:837–845 (1993)). Similarly, redD, which is linked to red biosynthetic genes, is required for expression of at least some red genes. ActII-ORF4 and RedD have been termed pathway-specific activators, and numerous antibiotic biosynthetic gene clusters in a variety of streptomycetes require the function of a genetically-linked pathway-specific activator for expression.

In addition to genes whose products specifically regulate the expression of one of the antibiotic gene clusters, a number of loci have been identified which contain genes that globally regulate more than one of the antibiotic biosynthetic clusters. Mutations in some of these, the bld loci, pleitropically block the synthesis of all four antibiotics as well as the production of sporulating aerial hyphae (Champness, W. C., J. Bacteriol. 170:1168–1174 (1988)). Other genes including abaA (Fernandez-Moreno, M. A., et al., J. Bacteriol. 174:2958–2967 (1992)), afsQ1-Q2 (Ishizuka, H., et al., J. Bacteriol. 174:7585–7594 (1992)) and afsR-K-R2 (Stein, D., et al., J. Bacteriol. 171:2258–2261 (1989)), play a role in the regulation of two or three of the antibiotics.

Mutations in two loci, absA (Adamidis, T., et al., J. Bacteriol. 172:2962–2969 (1990)) and absB (Adamidis, T., et al., J. Bacteriol. 174:4622–4628 (1992)) are known to block the synthesis of all four antibiotics, while having no pleiotropic effects upon morphological development. In addition suppressors of absA mutations (sab) exist which restore antibiotic synthesis to normal or even greater than normal levels. Thus the prior art has presumed that modification of the absA gene interrupts antibiotic production.

OBJECTS

It is therefore an object of the present invention to provide bacteria containing foreign DNA which allows hyperproduction of antibiotics, particularly in Streptomyces by disruption of the absA gene. Further, it is an object of the present invention to provide a method which allows the bacterium to be modified to hyperproduce the DNA.

Further, it is an object of the present invention to provide a method for modification of the absa gene which is relatively easy to perform. These and other objects will become increasingly apparent by reference to the following description and the drawings.

BRIEF DESCRIPTION OF DRAWINGS

FIGS. 1A and 1B are restriction maps of the insert in pWC3151. FIG. 1A—A restriction map of the insert in pWC3151 is shown along with the positions of the four ORFs identified in this application. FIG. 1B—RS100 was created by cloning the 3.2 kb XhoI fragment into KC516. The 2 kb BamHI fragment was introduced into KC516 to generate RS300 and the low copy number, self mobilizing plasmid pIJ922 to generate pCB200. pCB620 was created by subcloning the 3.2 kb BamHI/PstI fragment into pIJ922 (via the polylinker of pIJ2925, (Janssen, G. R., et al., Gene 124:133–134 (1993)). pCB395 was created by subcloning the 3.8 kb SacI/PstI fragment into pIJ2925 and then replacing the 1.45 kb XhoI/BamHI fragment with a cassette containing the ermE gene. The 1.45 kb XhoI/BamHI fragment, which is internal to absA1, was ligated into the XhoI/BglII sites of KC516 to create RS500. Restriction sites: A, apaI; B, BamHI; Bg, BglII; P, PstI; S, SacI; X, XhoI.

FIG. 2A—Recombination at position I would result in an Abs$^+$ (C410) phenotype, while recombination at position II would result in an Abs$^-$ (C411) phenotype. FIG. 2B—As the RS100 fragment spanned the absA mutations some of the prophage released from the lysogens had recombined at position I and therefore picked up the absA1-542 mutation on the phage genome, generating RS120. FIG. 2C—Any phage able to create Abs$^-$ lysogens would have to be carrying the absA1-542 mutation and recombine at position I.

FIGS. 4A to 4D show nucleotide sequence of the absA locus (SEQ ID NO:6) and the predicted amino acid sequence for the gene products of absA1-A2(SEQ ID NOS:1–2), d7 (SEQ ID NO:3) and d9 (SEQ ID NO:4) shown below the nucleotide sequence.

—FIG. 5A—The J1501 colonies have a regular domed-shaped surface which is covered with aerial hyphae and mature, grey colored, spore chains. FIG. 5B—The isolated colonies of C420 have an irregular crenulated surface which is only sparsely covered with aerial hyphae and mature spore chains. The C420 spores were viable and appeared, in phase contrast microscopy, indistinguishable from J1501 spores. The severity of the morphological phenotype was dependent upon the colony density on the agar plate, with the most densely populated areas showing colony morphology more reminiscent of the parent strain, but the more isolated colonies (as illustrated in the plate) showing the pronounced crenulated phenotype. The C420 colonies were also routinely smaller in diameter than those of their corresponding parent J1501.

DESCRIPTION OF PREFERRED EMBODIMENTS

Figure 2A:
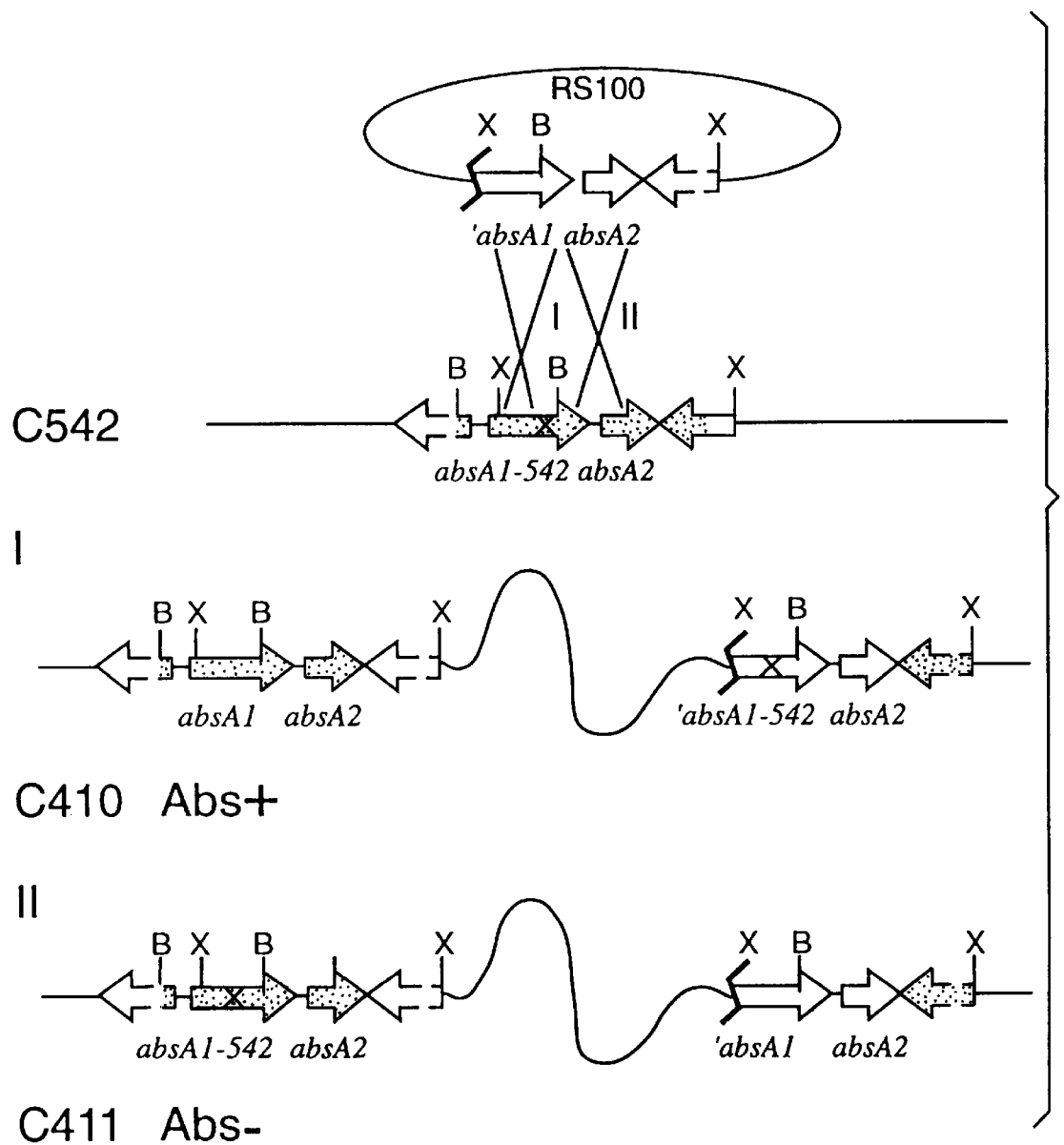
FIGS. 2A, 2B and 2C show the XhoI fragment in RS100 spanning all four absA mutations. The shading indicates those ORFs likely to be expressed based on sequence analysis discussed below.

The present invention relates to a *Streptomyces sp.* which produces an antibiotic and having an absA homologous locus of chromosomal DNA which encodes a histidine kinase and response regulator which has been modified by deletion of a segment of DNA of the absA locus and insertion of a foreign DNA which encodes a protein.

Further, the present invention relates to a *Streptomyces sp.* which produces an antibiotic and having a defined deletion in an absA homologous locus of chromosomal DNA which encodes a histidine kinase and response regulator.

The present invention also relates to a chromosomal DNA of a Streptomyces containing a segment of foreign DNA in place of a segment of DNA of absA.

The present invention also relates to a method for producing a *Streptomyces sp.* which produces an antibiotic and having a defined deletion in an absA homologous locus of chromosomal DNA which encodes a histidine kinase and response regulator which comprises deleting a segment of DNA of the absA locus.

Finally the present invention relates to a method for producing a *Streptomyces sp.* which produces an antibiotic and having an absA homologous locus of chromosomal DNA which encodes a histidine kinase and response regulator which has been modified by deletion of a segment of DNA of the absA locus of chromosome DNA and insertion of a foreign DNA which encodes a protein in the *Streptomyces sp.* which comprises exchanging a segment of DNA of the abs locus with a foreign DNA by cross-over transformation of the foreign DNA into chromosomal DNA of the *Streptomyces sp.*

The Streptomyces include:
*Streptomyces cromonospora*
*Streptomyces hygroscopicus*
*Streptomyces halstedii*
*Streptomyces erythreus*
*Streptomyces mediterranei*
*Streptomyces aureofaciens*
*Streptomyces venezuelae*
*Streptomyces spheroides*
*Streptomyces cinnamonensis*
*Streptomyces albus*
*Streptomyces caespitosus*
*Streptomyces avermitilis*
*Streptomyces parvulus*
*Streptomyces antibioticus*
*Streptomyces azureus*
*Streptomyces griseus*
*Streptomyces clavuligeris*
*Streptomyces lavendulae*
*Streptomyces lincolnensis*
*Streptomyces curacoi*
*Streptomyces fradiae*
*Streptomyces rimosus*
*Streptomyces peucetius*
*Streptomyces lividans*

SEQ ID NOS:1 and 2 show the sequence of absi and abs2. *Streptomyces coelicolor* (C421; Table 1) is deposited as ATCC 55927 on Jan. 29, 1997 with the American Type Culture Collection, 12301 Parklawn Drive, Rockville, Md. 20852. The culture is freely available upon request by name and deposit number. C421 is essentially the same as C420.

The cloning and characterization of the absA locus is described and evidence is presented that the absA signal transduction pathway normally acts as a global negative regulator of antibiotic synthesis in *S. coelicolor*.

Materials and Methods

Growth Conditions R2YE was used for growth on plates unless otherwise indicated. Thiostrepton was added to a final concentration of 10 μg/ml where indicated. YEME medium (Hopwood, D. A., et al., Genetic manipulations of Streptomyces; a laboratory manual. The John Innes Foundation, Norwich, U.K. (1985)) was used for liquid growth. Incubation conditions for cells growing on solid substrates or in liquid culture were as described. Spores were harvested and stored as previously described. E. coli was grown on L-agar or in L-broth.

Plasmids used and DNA Manipulations. The isolation and manipulation of Streptomyces plasmid or chromosomal DNA was performed according to the procedures described in Hopwood et al, Genetic manipulations of Streptomyces; a laboratory manual. The John Innes Foundation, Norwich, U.K. (1985). Mini-prep DNA from the C542 transformants was prepared from overnight cultures grown on cellulose acetate discs on L-agar. The mycelium was gently removed from the surface of the plates before the DNA was isolated using standard procedures.

Construction of a PIJ922 Library and conjugal transfer. The library was prepared by size fractionating Sau3A partially digested J1501 chromosomal DNA on a sucrose gradient. DNA fragments in the 10–30 kb size range were isolated and ligated into the unique, CIAP dephosphorylated, BamHI site of the SCP2* based vector pIJ922. The library was used in a PEG-assisted transformation of strain M124. Approximately $3 \times 10^4$ transformants were selected and patched onto R2YE plates. Following sporulation, colonies were replicated onto lawns of C542 spores which had been seeded onto R5 plates. After sporulation, these plates were replicated onto a minimal medium which selected for exconjugants (i.e. against the M124 genotype (cysD18, proA1, argA1) but for the C542 genotype (hisA1, ura1, strA1) and the thiostrepton resistance associated with the plasmid).

Antibiotic assays. Assays for the detection of actinorhodin, undecylprodigiosin, CDA and methylenomycin were performed as described in Adamidis, et al., (J. Bacteriol 172:2962–2969 (1990)). For methylenomycin assays, a C542-derivative carrying the methylenomycin-encoding, plasmid SCP1 was used: this strain was constructed by crossing SCPL from strain M138 (Table 1).

TABLE 1

Bacterial Strains

| Strain | Genotype | Reference |
|---|---|---|
| S. coelicolor A3(2[b]) | | |
| J1501 | hisA1 uraA1 strA1[a] | |
| C505 | absA505 hisA1 uraA1 strA1[a] | b |
| C542 | absA542 hisA1 uraA1 strA1[a] | b |
| C554 | absA554 hisA1 uraA1 strA1[a] | b |
| C577 | absA577 hisA1 uraA1 strA1[a] | b |
| M138 | argA1 proA1 cysD18 SCP1 | |
| M145 | prototroph[a] | |
| M124 | cysD18 proA1 argA1[a] | |
| C410 | absA542::RS100 hisA1 uraA1 strA1[a] | This work |
| C411 | absA542::RS100 hisA1 uraA1 strA1[a] | This work |
| C412 | absA::RS110 hisA1 uraA1 strA1[a] | This work |
| C413 | absA::RS120 hisA1 uraA1 strA1[a] | This work |
| C414 | absA::RS120 hisA1 uraA1 StrA1[a] | This work |
| C415 | absA::RS130 hisA1 uraA1 strA1[a] | This work |
| C416 | absA::RS140 hisA1 uraA1 strA1[a] | This work |
| C417 | absA505::RS300 hisA1 uraA1 strA1[a] | This work |
| C418 | absA505::RS310 hisA1 uraA1 strA1[a] | This work |
| C419 | absA::RS120[a] | This work |
| C420 | ΔabsA1::ermE hisA1 uraA1 strA1[a] | This work |
| C421 | ΔabsA1::ermE[a] | This work |
| C430 | ΔabsA2::RS500 hisA1 uraA1 strA1[a] | This work |
| 1501/KC900 | actI::KC900 hisA1 uraA1 strA1[a] | c |
| C425 | ΔabsA1 actI::KC900 hisA1 uraA1 strA1[a] | This work |

TABLE 1-continued

Bacterial Strains

| Strain | Genotype | Reference |
|---|---|---|
| S. lividans | | |
| 1326 | | |
| E. coli | | |
| ET12567 | | |

[a]SCP1⁻, SCP2⁻ two indigenous plasmids of S. coelicolor, SCP1 contains the biosynthetic loci for the antibiotic methylenomycin.
[b]Adamidis, T., et al., J. Bacteriol. 172:2962–2969 (1990).
[c]Bruton, C., et al., Bio/Technology 9:652–656 (1991).

absA⁺ clones (e.g. pWC3151) were then crossed into C542 SCP1⁺, with selection for thio[r]. For comparisons of actinorhodin and undecylprodigiosin production for C420 and J1501, the strains were grown on cellophane discs for 75 hours at which time the mycelium was harvested and resuspended in 6 ml of water, with 3 ml being used for each antibiotic assay.

Construction of lysogens in S. coelicolor and the harvesting of excised prophage for marker exchange experiments. Actinophage suspensions were prepared according to the protocols in Hopwood et al (1985). Spores of the host strain were plated onto R5 medium and an aliquot of the phage suspension was spotted onto the lawn of spores. Following sporulation, the plates were replicated onto selective minimal medium that contained thiostrepton at 20 $\mu$gml$^{-1}$. The phenotypes of thiostrepton resistant colonies were characterized. The genotype of lysogens was verified by Southern blot analysis of digested chromosomal DNA, which was hybridized to various probes from the absA locus. Excised phage were harvested by replicating plates of the lysogen onto DNA plates overlaid with S. lividans-seeded SNA, soaking out phage into DNB and then filtering the suspension through a 0.2 $\mu$m filter. The phage suspension was then screened for phage with the correct genotype.

DNA Sequencing. For DNA sequencing the dideoxy-chain termination method was used (Lark Sequencing Technologies Inc.) 7-deaza dGTP or 7-deaza dITP was used, if necessary, to resolve severe GC band compressions. DNA templates were generated using ExoIII digestion and cloned into Bluescript vectors. Every part of the sequence was determined at least twice in both directions. For sequence analysis the Wisconsin GCG package was used. The sequence reported here has been deposited in the GenBank data base, accession no. U51332.

Construction of the absA1 null mutants C420 and C421. The 3.7 kb SacI/PstI fragment was subcloned from pWC3151 into the Bluescript vector pSK+ and from there into pIJ2925. The 1.4 kb XhoI/BamHI fragment, which encodes amino acids 47 through 502 of the absA1 gene, was replaced by the ermE gene (Bibb, M. J., et al., Gene 41:357–368 (1986)), inserted such that the transcription of ermE was opposite to that of the absA locus. This construct was released as a BglII fragment and cloned into the BamHI site of pIJ963, creating pCB395 (FIG. 1). This plasmid was passaged through the methylase deficient E. coli strain ET12567 (Table 1). The DNA extracted from this strain was used to transform the protoplasts of two strains: J1501 (the auxotrophic parent strain for the original absA mutants) (Adamidis, T., et al., J. Bacteriol. 172:2962–2969 (1990)); and M145 (a prototrophic wild type strain). Transformants were selected for resistance to both erythromycin and hygromycin; this would select for single crossovers. Spores were harvested from representative transformants and plated onto non-selective medium. Once these colonies had sporulated, they were replicated onto medium containing either erythromycin or hygromycin. From this screen Hyg$^s$Ery$^r$ were isolated. Chromosomal DNA, digested with KpnI and XhoI and probed with flanking regions of the absA1 gene, contained the fragments predicted for the pattern of an ermE disruption of absA1 (data not shown).

XylE Enzyme Assays. The growth conditions and assay techniques for the KC900 and KC902 lysogens were the same as for XylE assays described, except the spores were placed upon SPMR medium. The KC900 phage contains a fragment internal to the actI coding region and creates lysogens through homologous recombination with actI. Thus it creates a single copy transcriptional fusion of the acti promoter to the reporter gene xylE (Bruton, C., et al., Bio/Technology 9:652–656 (1991)). Spores were incubated for various lengths of time on plates of SPMR and then harvested and each sample was assayed twice for XylE activity.

Results

Cloning a sequence that restores antibiotic production to absA mutants. The original absA mutants were isolated by taking advantage of the fact that two of the antibiotics are pigmented. The pigment deficient phenotype of the absA mutants is dramatically distinct from that of the deeply pigmented parental strain J1501 and complementing clones should restore the color. However, initial attempts to isolate complementing DNA were complicated by two phenomena. First, suppressive sab mutations, which create an Abs$^+$ phenotype, arose spontaneously in the absA mutant background at a frequency such that sab pseudo-revertants were reproducibly present at a frequency of approximately 0.1% in absA protoplasts preparations. Second, absA mutant protoplasts transformed at a frequency approximately 25-fold lower than either the wild type strain J1501 or the sab pseudo-revertant strains. The impact of these two factors was that the background level of phenotypically Abs$^+$ transformants arising after introduction of a cloning vector containing no insert was as high as 2.5%.

To circumvent these problems, a cloning scheme was employed based on the introduction of a library by conjugal transfer of the self-mobilizing plasmid pIJ922. After mating into the absA strain C542 (Table 1), clones which gave Abs$^+$ or pigmented patches, with approximately wild type levels of pigment, were isolated. When used to transform protoplasts of C542, eight independent clones, which had been identified by the mating procedure, reproducibly conferred the Abs$^+$ pigmented phenotype. The putative absA$^+$ clones were also introduced into other absA mutants C505, C554 and C577 (Table 1), resulting in production of antinorhodin and undecylprodigiosin.

When tested for the ability to restore biosynthetic capacity of CDA (Materials and Methods), the putative absA clones were all found to restore antibiotic biosynthesis to wild type levels (data not shown). Two representative clones were chosen for the methylenomycin assay (Materials and Methods) and were shown to restore biosynthetic capacity for this antibiotic as well (data not shown). Thus the putative absA clones globally restored antibiotic synthesis to absA mutant strains.

Preliminary restriction mapping of the putative absA clones revealed that four of the clones contained a comigrating 3.2 kb XhoI fragment, suggesting that all clones came from the same region. A representative clone, pWC3151 (Table 2), was chosen for further study.

TABLE 2

Plasmids and Bacteriophage

| Description | | Reference |
|---|---|---|
| Streptomyces plasmids | | |
| pIJ922 | SCP2* based low copy number plasmid | |
| pWC3151 | pIJ922 carrying 11.5 kb complementing insert | This work |
| pCB620 | pIJ922 carrying 3.2 kb BamHI/PstI insert | This work |
| pCB200 | pIJ922 carrying 1.95 kb BamHI insert | |
| E. coli plasmids | | |
| pSK+/pKS+ Bluescript | | Stratagene |
| pIJ2925 | pUC19 derivative with modified polylinker | a |
| pIJ963 | pIJ2925 containing hyg | |
| pIJ395 | pIJ963 containing SacI/PstI insert | This work |
| Streptomyces phages | | |
| KC516 | φC31 derived actinophage, att$^-$ c$^+$ | |
| KC900 | actI::xylE transcriptional fusion, att$^-$c$^+$ | b |
| KC902 | redX::xylE transcriptional fusion, $^{att-c}$+ | c |
| RS100 | KC516 carrying 3.2 kb XhoI insert | This work |
| RS300 | KC516 carrying 1.95 kb BamHI insert | This work |
| RS500 | KC516 carrying 1.45 kb XhoI/BamHI insert | This work |

$^a$Janssen, G. R., et al., Gene 124:133–134 (1993)
$^b$Bruton, C., et al., Bio/Technology 9:652–656 (1991).
$^c$Guthrie, E. P., et al., J. Bacteriol. 172:6189–6193 (1990).

Restriction mapping of the cloned insert revealed that the 3.2 kb XhoI fragment lay in the center of the approximately 11.5 kb insert sequence (FIG. 1). Southern blot hybridizations revealed that at least a portion of this 3.2 kb XhoI fragment was shared by six of the remaining seven clones. A seventh clone, pWC3146, showed no hybridization under stringent conditions as will be reported elsewhere.

Figure 3:
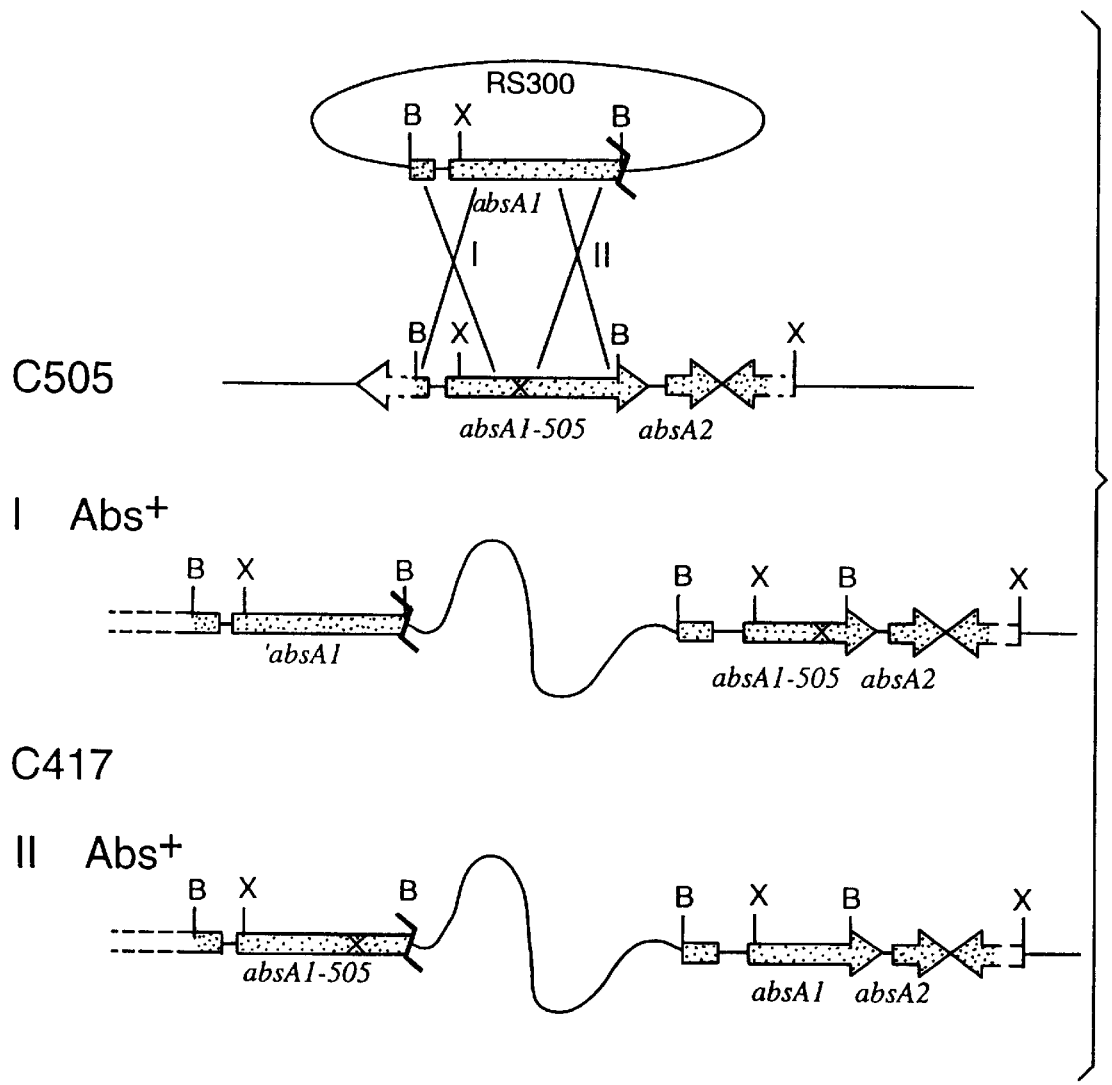
FIG. 3 shows the 2 kb BamHI fragment spanning the absA mutations thus placing all four of the mutations in absA1. The shading is as discussed in FIG. 2 legend. Marker exchange experiments were performed (See FIGS. 2B and 2C) with phage released from C417 and the absA1-505 mutant allele was cloned in the phage RS310.

Marker rescue of absA mutations in the chromosome. If the 3.2 kb XhoI fragment contained at least part of the absA locus then recombination between the XhoI fragment and a mutant absA gene in the chromosome might give rise to some absA$^+$ recombinants due to marker rescue. To test for marker rescue the XhoI fragment was cloned into the ΔattP temperate actinophage KC516, creating RS100 (FIG. 1). Because it lacks an attP region, lysogens resulting from infection by RS100 should be due to homologous recombination between the XhoI fragment and the corresponding region in the chromosome. If the clone overlaps the region of the absA mutation some of these recombinants should Abs$^+$. Approximately 50% of the lysogens produced pigment, the other lysogens retained the Abs$^-$phenotype. Similar results were obtained when RS100 was used to create lysogens in strains containing the other absA mutations. A straightforward interpretation of this data was that the 3.2 kb XhoI fragment spanned the region on the chromosome that contained the absA mutations but contained only one end of the sequence encoding the function altered by absA mutations (FIG. 2A). To identify fragments containing the entire absA encoding sequence, fragments overlapping the 3.2 kb XhoI fragment were also cloned into the phage. A 1.95 kb BamHI fragment that shares a 1.45 kb overlap with the XhoI fragment (FIG. 1), was able to restore the Abs$^+$ phenotype to 100% of lysogens in each of the four strains carrying an absA mutation (FIG. 3). In addition, a plasmid containing the 1.95 kb BamHI fragment, pCB200 (FIG. 1), restored the Abs$^+$ phenotype to all four absA mutants. These results suggested that the 1.95 kb BamHI fragment spanned the sites of the absA mutations on the chromosome and included sufficient coding information to produce the functional protein.

Marker exchange demonstrated that the complementing sequence encodes the absA⁺ allele.

Figure 2B:
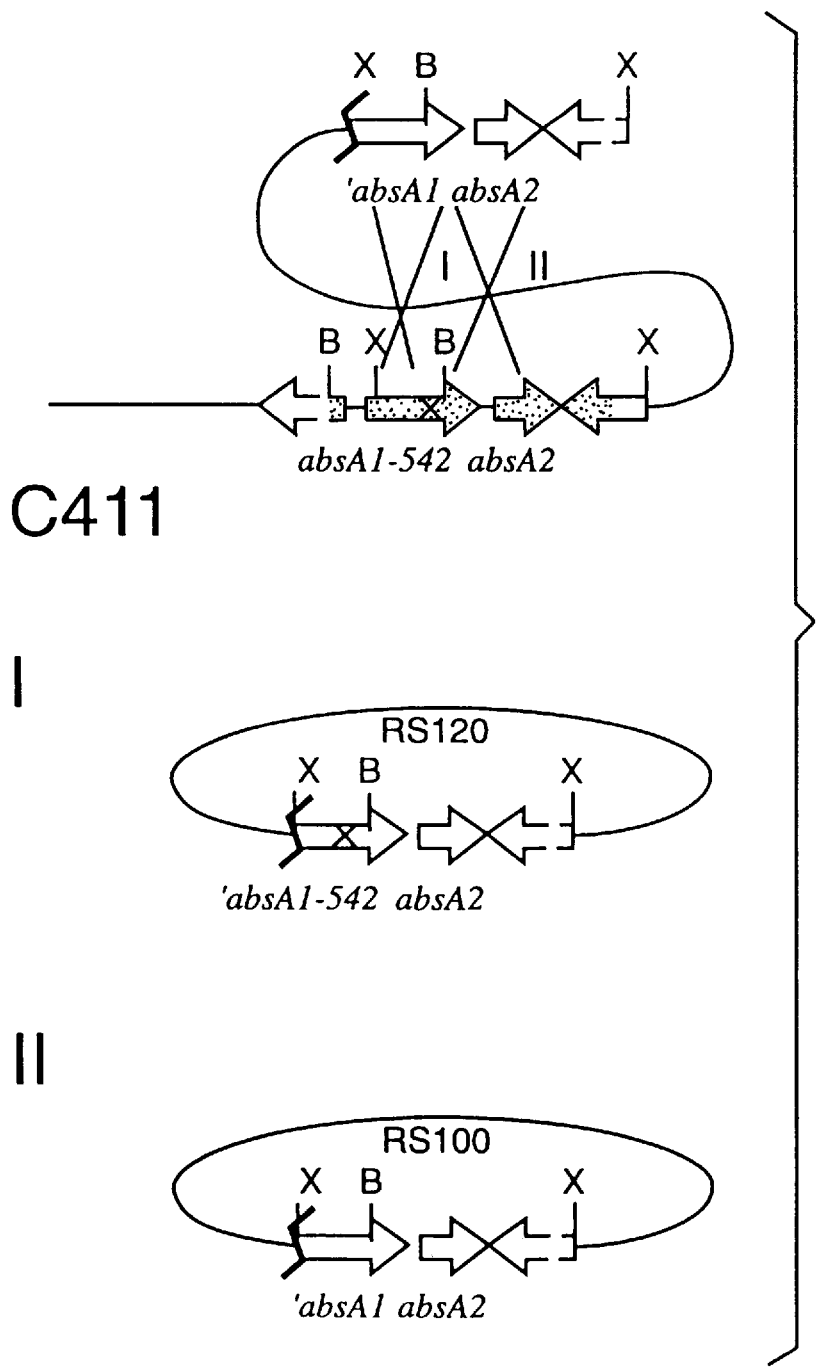
Figure 2C:
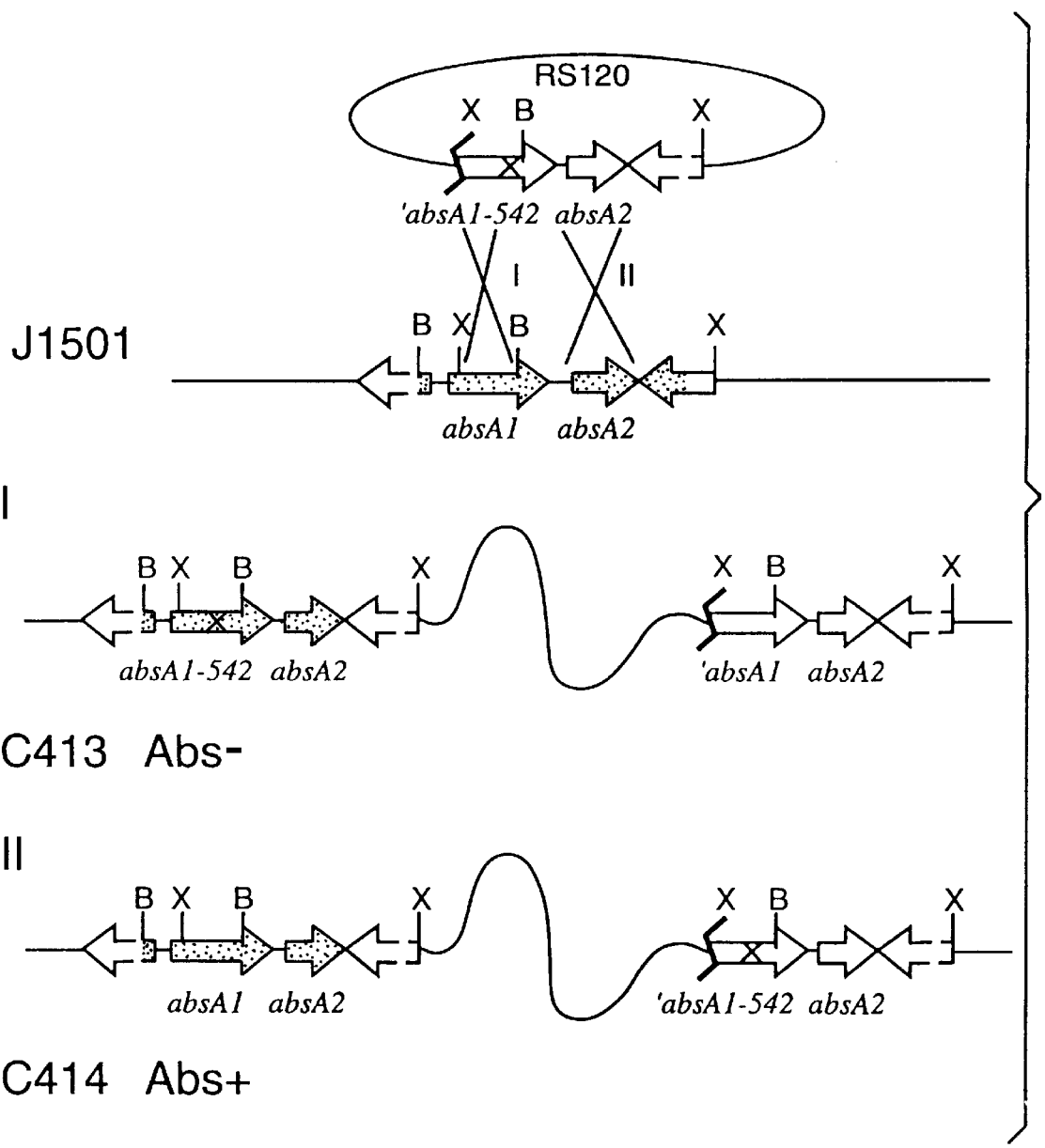

The possibility remained that the clones contained a sequence with suppressive capacity and not the bona fide absA locus. This possibility could be eliminated if absA mutations could be crossed onto the clone. To determine if any of the phage released from the lysogens now had the absA mutant allele instead of the wild type allele the phage were harvested (FIG. 2B) and used to lysogenize the Abs⁺ J1501 strain; approximately 50% of the lysogens were Abs⁻(FIG. 2C). In contrast, stocks of RS100 introduced into J1501 produced no Abs⁻lysogens of several hundred tested.

An additional experiment indicated that all four absA mutations lay within the 1.95 kb BamHI region. To demonstrate this, phage were harvested from lysogen C417 and screened for phage that carried the absA505 allele (Materials and Methods). These phage could not be screened for in J1501 as all lysogens produced from either RS300 or RS310 (absA505) would be Abs⁺. However, the phage were distinguished when introduced into the absA mutant C505, where RS300 produced Abs⁺ lysogens and RS310 produced Abs⁻ lysogens, a result that could occur only if the RS300 insert spanned the absA505 mutant site.

Correspondence of the genetic and physical map locations of the absA locus. Additional proof that the cloned sequence encoded the absA locus came from mapping the cloned DNA on the *S. coelicolor* chromosome. A combined physical-genetic AseI chromosomal map has recently been constructed for *S. coelicolor* (strain M145) by pulsed-field gel electrophoresis. This allowed location of the 3.2 kb XhoI fragment of RS100 on the chromosome. A ³²P labeled probe hybridized to AseI fragment E (data not shown). This physical location of the XhoI fragment on the chromosomal map, at fragment E, correlated with the previously defined map position of the absA locus in the 10 o'clock region of the genetic map (Adamidis, T., et al., J. Bacteriol 172:2962–2969 (1990)).

Nucleotide sequence and identification of the absA1 and absA2 genes. The 1.95 kb BamHI fragment was sequenced. Computer-aided analysis (Materials and Methods) of the sequence predicted two divergent ORFs (FIGS. 4A to 4D). The smaller partial ORF, designated d7, was predicted to start at the ATG codon at nucleotides 310 to 312, with the 3' end of the gene being downstream of the BamHI site. The larger, divergent, ORF was predicted to start at the ATG start codon at nucleotides 447 to 449. This second ORF spanned the 1.45 kb XhoI/BamHI region that contained the absA mutations. This gene was designated absA1. Because there were no stop codons in this reading frame before the BamHI site, the sequence of the downstream 1.2 kb BamHI/PstI fragment was determined and a stop codon was found at nucleotides 2160 to 2162 (FIGS. 4A to 4D). A third ORF, downstream of absA1 and transcribed from the same strand as absA1, started at the ATG codon at nucleotides 2181 to 2183. The 3' end of this gene was defined by the stop codon at nucleotides 2847 to 2849. This ORF was designated absA2 because of the relationship of its predicted product and that of the absA1 gene (see below). The stop codon for absA2 is overlapped by a second stop codon, nucleotides 2846 to 2848, for a predicted convergent ORF, designated d9, which is truncated at nucleotide 3216.

The absA locus encodes a two-component signal transduction system. A computer aided search of the GenBank EMBL databases revealed that AbsA1 showed sequence similarities to eubacterial histidine kinases (Parkinson, J. S., et al., Ann. Rev. Genet. 26:71–112 (1992)), particularly to the UhpB/DegS sub-group that also contains ComP, NarQ and NarX (Parkinson, J. S., et al,. Ann. Rev. Genet. 26:71–112 (1992)) (Brian, P., et al., J. of Bacteriology, p. 3221–3231 (1996)). The similarities between these proteins are predominantly limited to several conserved domains, the most notable of which is centered around the autophosphorylated histidine (Parkinson, J. S., et al., ann. Rev. Genet. 26:71–112 (1992)). It is predicted, from the sequence alignments, that the histidine at residue 202 is part of this conserved histidine phosphorylation domain in AbsA1 (Parkinson, J. S., et al., Ann. Rev. Genet. 26:71–112 (1992)) (Brian, P., et al., J. of Bacteriology, 3221–3231 (1996)). There is a second conserved domain centered around an asparagine residue (Parkinson, J. S., et al., Ann. Rev. Genet. 26:71–112 (1992)), that aligns with the AbsA1 asparagine residue at position 314 (Brian, P., et al., J. of Bacteriology, 3221–3231 (1996)). The COOH terminus of the AbsA1 protein shows little or no sequence similarity with the other histidine kinases and is longer than comparable regions in most histidine kinases. The COOH termini of the histidine kinases are variable, possibly because of the variety of functions performed by the various histidine kinases (Parkinson, J. S., et al., Ann. Rev. Genet. 26:71–112 (1992)). The COOH terminal 69 amino acids of AbsA1 were not required to complement the absA mutant alleles (FIG. 3). Like many histidine kinases the amino terminus of AbsA1 contains several hydrophobic domains that may be involved in spanning the membrane of the cell (Parkinson, J. S., et al., Ann. Rev. Genet. 26:71–112 (1992)).

The AbsA2 polypeptide showed sequence similarities to members of the UhpA/DegU sub-group of response regulator proteins that function with the UhpB/DegS group of histine-kinases (Parkinson, J. S., et al., Ann. Rev. Genet. 26:71–112 (1992)) (Brian, P., et al., J. of Bacteriology, 3221–3231 (1996)). For the response regulators, the regions with the highest sequence similarities are located in the amino terminal and central portions of the proteins; these include two conserved aspartate residues, one of which is the site of phosphorylation, and a conserved lysine residue (Parkinson, J. S., et al., Ann. Rev. Genet. 26:71–112 (1992)). Alignments of AbsA2 with the other response-regulators leads us to predict that residue 54 (Asp) is the probable site of phosphorylation (Brian, P., et al., J. of Bacteriology, 3221–3231 (1996)). The level of sequence identity is much higher among the response regulators than among histidine kinases (Parkinson, J. S., et al., Ann. Rev. Genet. 26:71–112 (1992)) and AbsA2 shows significant levels of identity, 39% with DegU and 35% with NarP, across its entire length.

Mutational disruption of the AbsA locus resulted in precocious hyperproduction of antibiotics. The apparent rarity of the original AbsA mutant isolates had suggested the possibility that the mutant strains might not contain null alleles (Adamidis, T., et al., J. Bacteriol 172:2962–2969 (1990)). To address this issue, a defined deletion was created in the absA locus. This was constructed by replacing amino acids 47 (Leu) to 502 (Arg) of the AbsA1 gene with the resistance marker ermE (Materials and Methods). This deletion-replacement construction deleted all conserved domains of AbsA1, leaving only 69 C-terminal amino acids and 46 N-terminal amino acids. This replacement construction would likely have a polar effect on expression of absA2. We have not yet determined whether absA2 is obligatorily cotranscribed with absA1, but the close linkage of the ORFs (FIGS. 4A to 4D) and precedent with other "two-component" gene pairs (Parkinson, J. S., et al., Ann. Rev. Genet. 26:71–112 (1992)) suggests that it may be. Transcription of ermE was opposite to that of absA1 and absA2, so read-through transcription would not transcribe absA2.

The visible phenotype and measurements of actinorhodin and undecylprodigiosin synthesis in a representative absA::ermE mutant strain designated C420 (Table 1), indicated that both actinorhodin and undecylprodigiosin were produced prematurely and much more abundantly in the absA1 null mutant in comparison to the parent strain J1501. In three replicate assessments of plate-grown cultures, actinorhodin production initiated 6 to 12 hours earlier in C420 and undecylprodigiosin production initiated 6 to 12 hours earlier. At 75 hours of incubation, the C420 culture produced five-fold increased actinorhodin and eight-fold increased undecylprodigiosin with respect to J1501 (0.74 mg vs. 0.14 mg/g of mycelium of actinorhodin and 0.83 mg vs. 0.11 mg/g of mycelium of undecylprodigiosin). C420 produced abundant calcium-dependent antibiotic, but the "zone-of-killing" assay used (Materials and Methods) did not conclusively demonstrate an increased rate of production in C420. Methylenomycin production was not assessed.

Figure 5A:
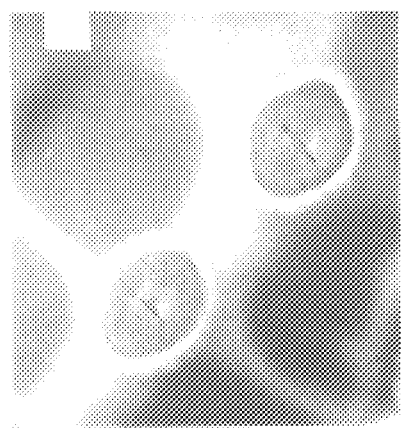
FIGS. 5A and 5B.
Figure 5B:
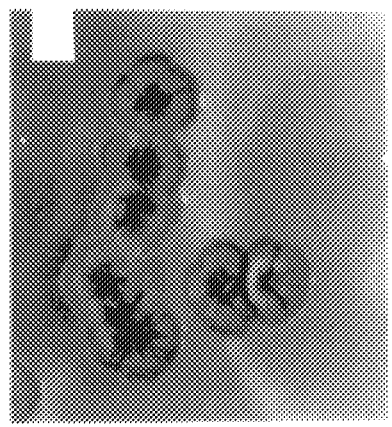

The colony morphology of the C420 colonies was also altered: the surface of the colony was highly crenulated and sporulating hyphae were sparse (FIG. 5B). In comparison to J1501, these mutants also show a marked deficiency in their transformation efficiency, comparable to the transformation deficiency described for the C542 protoplasts. These is no explanation for the transformation deficiency nor is it yet understood what the relationship is between the antibiotic production and morphological phenotypes of C420. To verify that all the phenotypes described for C420 were due solely to the disruption of the absA locus, plasmid PCB620 (FIG. 1) was introduced into this strain by transformation. Transformants were restored to the wild type phenotypes for all characteristics described above.

Figure 6:
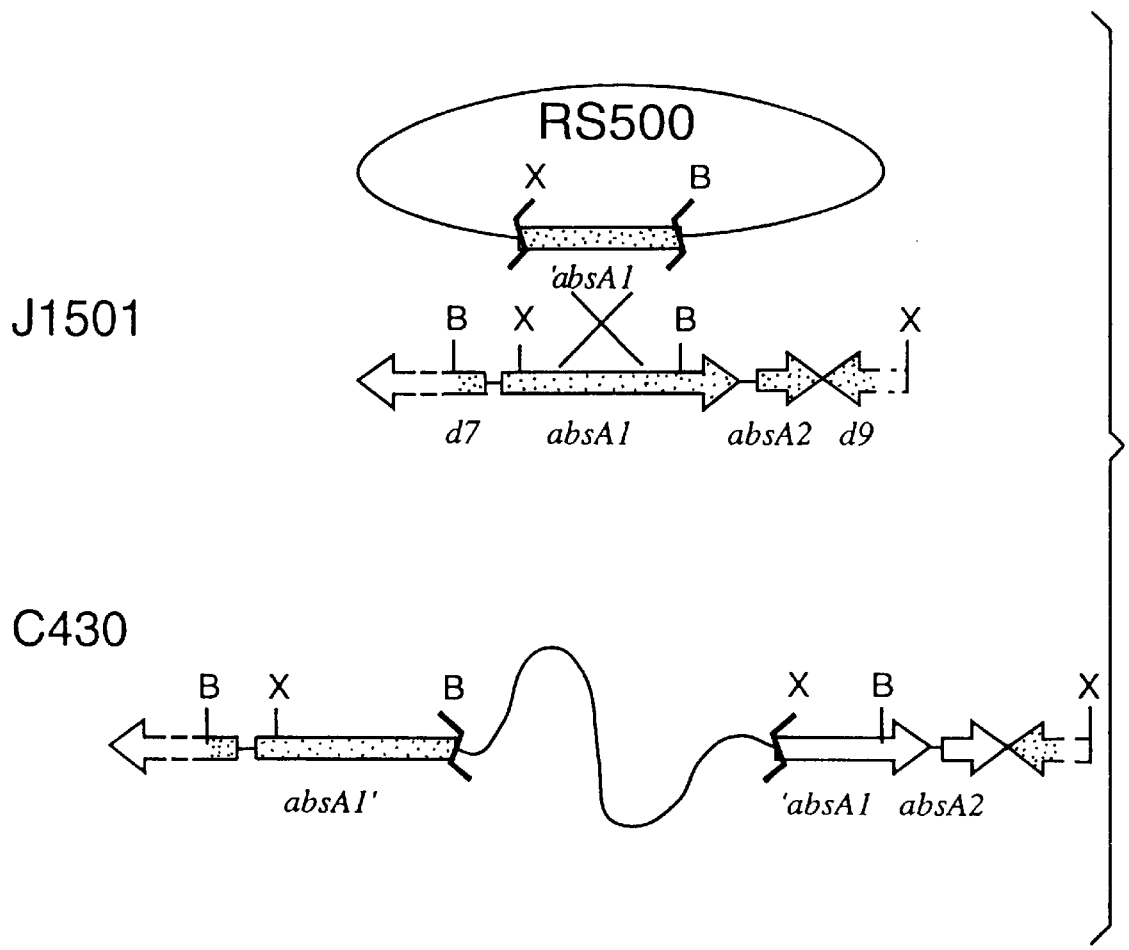
FIG. 6 shows disruption of the absA locus by integration of RS500. The shaded areas represent those ORFs thought to be transcribed in these constructs.

Disruption of absA2 alone may cause precocious overproduction of antibiotics. All aspects of the C420 phenotype were duplicated in a strain, C430, in which the absA locus was disrupted as shown in FIG. 6. To construct C430, the phage RS500, containing an insert internal to absA1 (FIG. 1), was introduced into J1501 by homologous recombination at the absA1 gene. C430 would express a truncated version of AbsA1, but it is expected that because the same truncated version of AbsA1 was sufficient for complementation of the absA1-505 mutant (as shown in FIG. 3), it is possible that the C430 mutant phenotype resulted from failure to express absA2.

Figure 7:
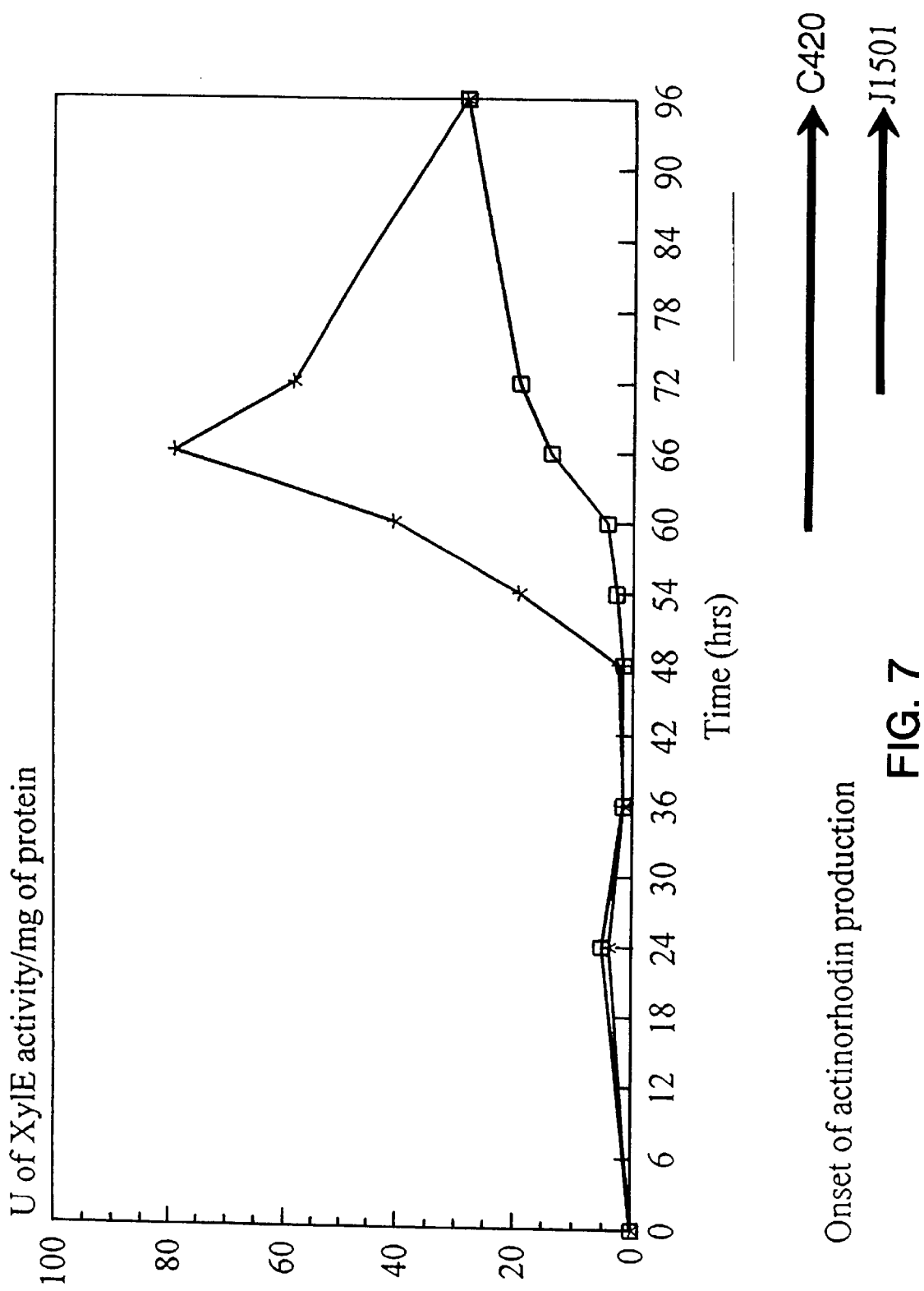
FIG. 7. Transcription of actI. This time course was repeated twice and the temporal difference in actT transcription between C420::KC900 (★) and J1501::KC900 (□) ranged between 6 to 12 hours for both time courses. The arrows at the base of the figure illustrate when actinorhodin was first produced during the assays.

Precocious production of actinorhodin correlated with premature transcription of antibiotic biosynthetic genes. To assess whether the increase in actinorhodin production in C420 was due to an increase in the transcription of the act biosynthetic genes, transcriptional fusions were constructed between an act biosynthetic promoter, actI, and the reporter gene xylE using the actinophage KC900 (Bruton, C., et al., Bio/Technology 9:652–656 (1991) Materials and Methods). The XylE activity of the C420::KC900 strain initiated between 48–54 hours after inoculation, on SPMR medium; this was consistently 6–12 hours before the onset of XylE activity from the J1501::KC900 strain. Also, the peak activity for C420::KC900 occurred earlier and was greater than for J1501::KC900 (FIG. 7). The onset of actinorhodin production was also assayed during the time course and showed a temporal difference for the onset of production corresponding to the difference seen in the XylE transcription assays (FIG. 7). Similar experiments were carried out using the less well characterized KC902 xylE fusion to the redy undecylprodigiosin biosynthetic locus (Guthrie, E. P., et al., J Bacteriol. 172:6189–6193 (1990)). In these experiments, XylE activity in C420::KC902 increased 6 to 12 hours earlier than in J1501::KC902. Peak XylE activity in C420::KC902 was approximately twenty percent higher than in J1501::KC902 (Data not shown). Because red transcripts are not well characterized, transcription from red genes, in the C420 strain, will require further characterization.

The absA1-542 and ΔabsA1::ermE mutant alleles caused identical phenotypes in a range of laboratory S. coelicolor strains. Much of the molecular genetic investigation of S. coelicolor antibiotic regulation has utilized two strains as representatives of "wild-type" antibiotic production and regulation characteristics: J1501 (Adamidis, T., et al., J. Bacteriol. 172:2962–2969 (1990); Adamidis, T., et al., J. Bacteriol. 174:4622–4628 (1992)). Therefore, we constructed absA542 carrying strains in J1501 and M145, named C413 and C419 respectively (Materials and Methods). To create C419 the absA542 allele was introduced into M145 on the phage RS120, (similarly to the protocol of FIG. 2C). C419, like C413 failed to produce any detectable actinorhodin, undecylprodigiosin or CDA (Methylenomycin production was not assessed since M145 lacks the methylenomycin-encoding plasmid SCP1). Also, there were no obvious deficiencies in the sporulation or growth of C419.

Using the same procedure as was used for the construction of C420 (Materials and Methods) the absA1::ermE allele was introduced into M145, creating C421. The phenotype of C421 was precocious hyperexpression of antibiotics, as has already been described for C420. Similarly, C421 displayed the crenulated surface morphology and transformation deficiencies described for C420. Thus the phenotypes seen in the M145 background are identical to those described for the absA alleles in a J1501 background.

Discussion

It has been shown that the absA-encoded signal transduction system exerts global control over production of the S. coelicolor antibiotics. The absA locus was first defined by mutations that globally blocked antibiotic synthesis. All four such mutations lie within absA1, which encodes a sensor-kinase. Downstream of absA1 lies a second ORF, absA2, which encodes the cognate response regulator for AbsA1. In stark contrast to the antibiotic nonproducing phenotype resulting from the original absA mutations, disrupted absA alleles, as exemplified in the C420 and C430 strains, cause an opposite effect on antibiotic synthesis—precocious overproduction. Early, increased accumulation of act and red transcripts correlates with the observable enhanced antibiotic synthesis in the C420 strain.

Fundamental studies on S. coelicolor physiology and genetics have utilized a number of laboratory strains. The choice of strain J1501 as the parent for mutant isolation schemes was based on its suitability for subsequent genetic analyses; its attributes include useful markers for genetic mapping studies and suitability as a host for phage and plasmid vectors. Furthermore, in contrast to some other S. coelicolor strains that exhibit variability in morphological and antibiotic phenotypes—a widely observed characteristic of Streptomyces spp. that is associated with chromosomal rearrangements—J1501 is phenotypically relatively stable. This attribute obviously facilitated mutant screens. But J1501 has recently been shown to have suffered deletion of as much as one-tenth of its genome. Clearly it was important to contrast the phenotypic effects of the mutant absA alleles in J1501 and other, undeleted strains. As shown above, both the absA542 blockage to antibiotics and the absA1::ermEeffected precocious synthesis of antibiotics occur when these alleles are transferred to another well characterized *S. coelicolor* strain.

The premature hyperexpression of antibiotics in C420 and C430 may be due to absence of the AbsA2 response regulator. Thus the absA two-component system may function as a negative regulator of antibiotic gene expression. Global negative regulators of *S. coelicolor* antibiotic biosynthesis other than absA have not been described, but it is not unprecedented for response regulators to function in negative as well as positive regulation. One such example is the DegS/U system from *B. subtilis*, in which the response regulator DegU plays multiple roles during the transition from exponential growth to stationary phase (Dahl, M. K., et al., J. Biol. Chem. 267:14509–14514 (1992)). The phosphorylated form performs dual functions: it represses srfA, which is involved in the production of the antibiotic surfactin; and it positively regulates degradative enzyme synthesis. The unphosphorylated form is also biologically active and plays a role in the acquisition of genetic competence. At present the exact mechanism of the AbsA-mediated negative regulation is not known. But as shown, AbsA signal transduction exerts its effects on transcription of the antibiotic genes, at least for actinorhodin and undecylprodigiosin. Additionally, the original absA mutation absA1-542 dramatically reduces the transcription of the actinorhodin pathway specific activator, actII4 and the undecylprodigiosin pathway specific activator, redD. In future work, exploration of the spectrum of possible phenotypes that can result from mutational alteration of the absA1-A2 genes will help to elucidate the regulatory mechanisms.

The absA signal transduction pathway is likely to be part of a complex interconnected regulatory web. The actI transcript appeared prematurely and reached a higher level in C420 than in J1501. But temporal regulation was not entirely lost, suggesting that additional regulatory elements can influence the transcription of the antibiotic biosynthetic loci. The existence of such a network of regulatory influences has been hinted at in other work. Other genes known to impact *S. coelicolor* antibiotic biosynthesis were discovered because of the observation that their overexpression increased actinorhodin and undecylprodigiosin production. These include afsQ1-Q2, which encode a two component system (Ishizuka, H., et al., J. Bacteriol. 174:7585–7594 (1992)), and the afsR-K-R2 locus, which encodes a serine-threonine kinase, a target phosphorylated protein; and Matsumoto, A., et al., Gene 146:47–56 (1994)) and a protein with some sigma factor domains. Either multiple copies of the response regulator afsQl (Ishizuka, H., et al., J. Bacteriol. 174:7585–7594 (1992)) or cloned regions from the afsR-K-R2 locus (Champness, W. C., et al., Gene 115:55–60 (1992)) restore actinorhodin and undecylprodigiosin production to the absA mutant strain C542; the mechanism of this suppression is not known. At least for the case of the afsR-K-R2 mediated suppression, it is clear that the absA542 blockage of the two other characterized antibiotics, CDA and methylenomycin is not reversed (Champness, W. C., et al., Gene 115:55–60 (1992)). The suppressive effect of cloned copies of these genes suggests functional intersection with the absA1-A2 pathway. Characterization of the suppressive clone pWC3146, identified in this application, may reveal another regulatory element that interacts with the absA signal transduction pathway.

The production of secondary metabolites is usually associated with the transition to stationary phase in eubacteria, so it is not surprising to discover that *S. coelicolor* uses signal transduction pathways to coordinate the expression of these regulons in response to their rapidly changing environments. In the last few years, several two-component signal transduction pathways have been shown to be involved in the regulation of secondary metabolism in other bacteria. Examples include *B. subtilis*, which uses the comA-P and degS-U systems to regulate expression of the antibiotic surfactin, hydrolytic enzymes and competence genes; *Pseudomonas fluorescens*, CHAO which uses the gacA response regulator to globally regulate secondary metabolism (Laville, J., et al., Proc. Nat. Acad. Sci. 89:1562–1566 (1992)) and *P. fluorescens* Pf-5 which uses apdA signal transduction system to regulate antibiotic production (Corbell, N., et al., J. Bacteriol. 177:6230–6236 (1995)). In other streptomycete, *S. peucetius*, the regulator DnrN regulates production of daunorubicin (Otten, S. L., et al., J. Bacteriol. 177:1216–1224 (1995)); a cognate sensor-kinase has not yet been identified. In contrast to absA-mediated global regulation, DnrN-mediated regulation is thus far known to affect production of only daunorubicin.

AbsA1 contains a hydrophobic N-terminus, suggesting that it responds to an external signal and that the production of antibiotics in *S. coelicolor* is intimately tied to the external environment of the colony. As yet there is no evidence as to what constitutes the signal molecule for the absA signal transduction pathway. Some clues regarding the nature of the absA signal molecule may come from the signal transduction pathways involved in the regulation of secondary metabolites in other bacteria. For example, the *B. subtilis* ComP and ComA proteins are thought to sense and transduce information regarding cell density. At least two oligopeptides are major components of an extracellular signal and ComP senses one of these, perhaps directly. A cell density signal is also important in antibiotic regulation in Erwinia and *Serratia spp.*, which can produce the β-lactam compound carbapenum. In these bacteria, it is molecules of an N-acyl homoserine lactone structure that act as autoinducers to signal cell density (Bainton, N. J., et al., Gene 116:87–91 (1992)). In these regulatory systems the sensing proteins are not two-component type systems, but rather are homologues of the LuxR protein (McGowan, S., et al., Microbiology 141:541–550 (1995)) which was discovered as a regulator of luciferase expression in luminescent marine bacteria. Homoserine lactone molecules also function in various Streptomyces species' sporulation and antibiotic production (Horinouchi, S., et al., Mol. Microbiol. 12:859–864 (1994)), but no evidence links these to absA signaling.

It has long been speculated that a greater understanding of the regulation of antibiotic synthesis would eventually lead to improvements in antibiotic yields (Chater, K. F., Bio/Technology 8:115–121 (1990)). The isolation and characterization of some of the regulatory elements from *S. coelicolor* has already made some of those goals possible. Further study of these regulatory mechanisms will not only lead to a greater understanding of the initiation of secondary metabolism in *S. coelicolor* but will also undoubtedly lead to the rational genetic design of actinomycetes that overproduce commercially important compounds.

The sequences of FIGS. 4A to 4D are shown in SEQ ID NOS: 1 through 7.

It is intended that the foregoing description be only illustrative of the present invention and that the present invention be limited only by the hereinafter appended claims.

We claim:

1. A *Streptomyces sp.* which produces an antibiotic and having an absA locus of chromosomal DNA which encodes a histidine kinase and response regulator which has been modified by deletion of a segment of the DNA of the absA locus and insertion of a foreign DNA which encodes a protein.

2. The *Streptomyces sp.* of claim 1 wherein the bacterium is a *Streptomyces coelicolor.*

3. The *Streptomyces sp.* of claim 1 wherein the bacterium is *Streptomyces coelicolor* deposited as ATCC 55927.

4. The *Streptomyces sp.* of any one of claims 1, 2 or 3 wherein a segment of foreign DNA is ermE DNA.

5. An isolated and purified DNA as set forth in FIGS. 4A to 4D.

6. A chromosomal DNA of a *Streptosyces sp.* containing a segment of foreign DNA in place of a segment of DNA of absA.

7. The DNA of claim 6 from *Streptomyces coelicolor.*

8. The DNA of claim 6 from *Streptomyces coelicolor* deposited as ATCC 55927.

9. The DNA of any one of claims 6, 7 or 8 wherein the foreign DNA is ermE DNA.

10. The DNA of any one of claims 6, 7 or 8 wherein the absA1 is as set forth in FIGS. 4A to 4D.

11. A method for producing a *Streptomyces sp.* which produces an antibiotic and having an absA locus of chromosomal DNA which encodes a histidine kinase and response regulator which has been modified by deletion of a segment of DNA of the absA locus of chromosome DNA and insertion of a foreign DNA which encodes a protein in the *Streptomyces sp.* which comprises exchanging a segment of DNA of the abs locus with a foreign DNA by cross-over transformation of the foreign DNA into chromosomal DNA of the *Streptomiyces sp.*

12. The method of claim 11 wherein the *Streptomyces sp.* is a *Streptomyces coelicolor.*

13. The method of claim 11 wherein the *Streptomyces sp.* is *Streptomiyces coelicolor* deposited as ATCC 55927.

14. The method of claim 11 wherein the DNA of the abs locus is as set forth in FIGS. 4A to 4D.

15. The method of any one of claims 11, 12 or 13 wherein the segment of foreign DNA is ermE DNA.

16. A *Streptomyces sp.* which produces an antibiotic and having a defined deletion in an absA locus of chromosomal DNA which encodes a histidine kinase and response regulator.

17. The bacterium of claim 16 which is *Streptomyces coelicolor* deposited as ATCC 55927.

18. A method for producing a *Streptomyces sp.* which produces an antibiotic and having a defined deletion in an absA locus of chromosomal DNA which encodes a histidine kinase and response regulator which comprises deleting a segment of DNA of the absA locus.

19. The method of claim 18 wherein the bacterium is *Streptomyces coelicolor* deposited as ATCC 55927.

20. A *Streptomnyces sp.* which produces an antibiotic and having an AbsA locus of chromosomal DNA which encodes a histidine kinase and response regulator which has been modified by disruption of a segment of the DNA of the abs locus so that there is hyperproduction of the antibiotic.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 571
( B ) TYPE: Amino Acid
( C ) STRANDEDNESS: Single
( D ) TOPOLOGY: Linear ( i i ) MOLECULE TYPE: Amino Acid ( i i i ) HYPOTHETICAL: No ( i v ) ANTI-SENSE: No ( v ) FRAGMENT TYPE:

( v i ) ORIGINAL SOURCE:
( A ) ORGANISM: Streptomyces coelicolor
( B ) STRAIN: N/A
( C ) INDIVIDUAL ISOLATE:
( D ) DEVELOPMENTAL STAGE:
( E ) HAPLOTYPE: N/A
( F ) TISSUE TYPE: N/A
( G ) CELL TYPE: unicellular organism
( H ) CELL LINE:
( I ) ORGANELLE:

( v i i ) IMMEDIATE SOURCE: N/A ( v i i i ) POSITION IN GENOME:

( i x ) FEATURE:
( A ) NAME/KEY: AbsA1
( B ) LOCATION:
( C ) IDENTIFICATION METHOD: deduced
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( K ) RELEVANT RESIDUES IN SEQ ID NO:

( x i ) SEQUENCE DESCRIPTION: SEQ ID NO:1:

```
Met His Arg Trp Gln Ala Val Arg Arg Arg Ile Glu
                    5                   10
Ser Leu Val Arg Val Leu Gly Ser Glu Arg Pro Phe
            15                  20
Thr Arg Arg Ala Asp Leu Val Leu Leu Leu Val Leu
25                  30                  35
Leu Val Pro Ser Ala Phe Ala Thr Gly Thr Leu Glu
            40                  45
Thr Ala Pro Val Ala Trp Leu Thr Ala Cys Leu Leu
    50                  55                  60
Ile Ala Ala Ala Val Val Val Gln Arg Thr Ala Pro
                    65                  70
Leu Leu Ser Leu Leu Leu Ala Ala Leu Leu Thr Leu
            75                  80
Phe Tyr Pro Trp Phe Gly Ala Asn Leu Trp Pro Ser
85                  90                  95
```

```
Met  Ala  Thr  Val  Val  Leu  Ser  Cys  Leu  Ala  Gly  Arg
               100                 105

Arg  Leu  Thr  Arg  Leu  Trp  Pro  Ala  His  Leu  Val  Phe
     110                      115                      120

Leu  Cys  Val  Ala  Ala  Ala  Gly  Leu  Leu  Leu  Val  Ala
                    125                      130

Thr  Val  Gly  Gln  Gly  Lys  Asp  Trp  Leu  Ser  Leu  Leu
               135                 140

Met  Thr  Glu  Phe  Val  Ala  Cys  Val  Leu  Pro  Trp  Trp
145                      150                      155

Ala  Gly  Asn  Trp  Trp  Ser  Gln  Arg  Thr  Ala  Leu  Thr
               160                 165

His  Ala  Gly  Trp  Glu  His  Ala  Glu  Gln  Leu  Glu  Trp
     170                      175                      180

Arg  Gln  Arg  Tyr  Ile  Ala  Asp  Gln  Ala  Arg  Met  Lys
                    185                      190

Glu  Arg  Ala  Arg  Ile  Ala  Gln  Asp  Ile  His  Asp  Ser
               195                 200

Leu  Gly  His  Glu  Leu  Ser  Val  Met  Ala  Leu  Leu  Ala
205                      210                      215

Gly  Gly  Leu  Glu  Leu  Ala  Pro  Gly  Leu  Ser  Asp  Pro
               220                 225

His  Arg  Glu  Ser  Val  Gly  Gln  Leu  Arg  Glu  Arg  Cys
     230                      235                      240

Thr  Met  Ala  Thr  Glu  Arg  Leu  His  Glu  Val  Ile  Gly
               245                 250

Leu  Leu  Arg  Glu  Asp  Pro  Asn  Pro  Ser  Leu  Thr  Pro
               255                 260

Ala  Asp  Glu  Ser  Val  Ala  Gln  Leu  Val  Arg  Arg  Phe
265                      270                      275

Gln  Arg  Ser  Gly  Thr  Pro  Val  Arg  Phe  Gln  Glu  Asp
               280                 285

Gly  Ala  Arg  Asp  Arg  Pro  Gly  Thr  Pro  Leu  Leu  Ser
     290                      295                      300

Asp  Leu  Ala  Ala  Tyr  Arg  Val  Val  Gln  Glu  Ala  Leu
                    305                      310

Thr  Asn  Ala  Ala  Lys  His  Ala  Pro  Gly  Ala  Pro  Ile
               315                 320

Asp  Val  Arg  Val  Thr  His  Thr  Ala  Asp  Glu  Thr  Val
325                      330                      335

Val  Ser  Val  Val  Asn  Glu  Arg  Pro  Glu  Arg  Gly  Gly
                    340                      345

Ser  Val  Pro  Ala  Ala  Gly  Ser  Gly  Ser  Gly  Leu  Ile
     350                      355                      360

Gly  Leu  Asp  Glu  Arg  Val  Arg  Leu  Ala  Gly  Gly  Thr
                    365                      370

Leu  Arg  Thr  Gly  Pro  Arg  Ala  Gly  Gly  Phe  Glu  Val
          375                      380

Tyr  Ala  Arg  Leu  Pro  Arg  Gly  Ala  Ser  Ser  Pro  Ser
385                      390                      395

Arg  Ser  Thr  Glu  Pro  Pro  Gly  Pro  Ala  Asp  Gly  Asp
               400                 405

Gly  Thr  Ala  Gly  Gly  Ser  Gly  Asp  Gly  Thr  Ala  Pro
```

```
                        410                            415                            420
Gly  Ala  Ala  Thr  Ala  Gly  Asn  Glu  Gly  Arg  Ala  Ala
                    425                            430

Ala  Ala  Ala  Ala  Asp  Leu  Pro  Ala  Pro  Ser  Gly  Pro
               435                      440

Trp  Arg  Ser  Ala  Ser  Arg  Ala  Ala  Leu  Leu  Arg  Thr
445                      450                          455

Arg  Ala  Arg  Ile  Arg  Arg  Asp  Ala  Arg  Arg  Ala  Ala
               460                      465

Leu  Ile  Pro  Ala  Val  Leu  Gly  Ala  Ala  Ile  Val  Ala
     470                      475                          480

Phe  Leu  Gly  Gly  Leu  Tyr  Val  Phe  Thr  Ser  Ala  Thr
                    485                          490

Thr  Ser  Leu  Ala  Pro  Glu  Asp  Tyr  Ala  Arg  Ile  Arg
          495                           500

Val  Gly  Glu  Thr  Arg  Ala  Asp  Leu  Ala  Pro  Ala  Leu
505                           510                     515

Pro  Glu  Arg  Arg  Ile  Lys  Lys  Pro  Pro  Pro  Val  Thr
               520                      525

Ser  Glu  Pro  Ser  Val  Pro  Ala  Gly  Thr  Thr  Cys  Glu
     530                           535                     540

Tyr  Tyr  Arg  Ala  Ser  Ser  Gly  Leu  Leu  Asp  Phe  Gly
                    545                           550

Gly  Ala  Met  Tyr  Arg  Leu  Cys  Phe  Lys  Asp  Asp  Val
          555                      560

Leu  Met  Ala  Lys  Asp  Thr  Leu
565                           570
```

( 2 ) INFORMATION FOR SEQ ID NO:2:

( i ) SEQUENCE CHARACTERISTICS:
        ( A ) LENGTH: 222
        ( B ) TYPE: Amino Acid
        ( C ) STRANDEDNESS: Single
        ( D ) TOPOLOGY: Linear ( i i ) MOLECULE TYPE: Amino Acid ( i i i ) HYPOTHETICAL: No ( i v ) ANTI-SENSE: No ( v ) FRAGMENT TYPE:

( v i ) ORIGINAL SOURCE:
        ( A ) ORGANISM: Streptomyces coelicolor
        ( B ) STRAIN: N/A
        ( C ) INDIVIDUAL ISOLATE: N/A
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: N/A
        ( I ) ORGANELLE: N/A ( v i i ) IMMEDIATE SOURCE: N/A ( v i i i ) POSITION IN GENOME: N/A ( i x ) FEATURE:
        ( A ) NAME/KEY: AbsA2
        ( B ) LOCATION:
        ( C ) IDENTIFICATION METHOD: deduced
        ( D ) OTHER INFORMATION:

( x ) PUBLICATION INFORMATION:

(A) AUTHORS:
(B) TITLE:
(C) JOURNAL:
(D) VOLUME:
(E) ISSUE:
(F) PAGES:
(G) DATE:
(K) RELEVANT RESIDUES IN SEQ ID NO:

(xi) SEQUENCE DESCRIPTION: SEQ ID NO:2:

```
Met Ile Arg Val Leu Leu Ala Asp Asp Glu Thr Ile Ile Arg Ala
                 5                  10                 15
Gly Val Arg Ser Ile Leu Thr Thr Glu Pro Gly Ile Glu Val Val
                20                  25                 30
Ala Glu Ala Ser Asp Gly Arg Glu Ala Val Glu Leu Ala Arg Lys
                35                  40                 45
His Arg Pro Asp Val Ala Leu Leu Asp Ile Arg Met Pro Glu Met
                50                  55                 60
Asp Gly Leu Thr Ala Ala Gly Glu Met Arg Thr Thr Asn Pro Asp
                65                  70                 75
Thr Ala Val Val Val Leu Thr Thr Phe Gly Glu Asp Arg Tyr Ile
                80                  85                 90
Glu Arg Ala Leu Asp Gln Gly Val Ala Gly Phe Leu Leu Lys Ala
                95                 100                105
Ser Asp Pro Arg Asp Leu Ile Ser Gly Val Arg Ala Val Ala Ser
               110                 115                120
Gly Gly Ser Cys Leu Ser Pro Leu Val Ala Arg Arg Leu Met Thr
               125                 130                135
Glu Leu Arg Arg Ala Pro Ser Pro Arg Ser Glu Val Ser Gly Glu
               140                 145                150
Arg Thr Thr Leu Leu Thr Lys Arg Glu Gln Glu Val Leu Gly Met
               155                 160                165
Leu Gly Ala Gly Leu Ser Asn Ala Glu Ile Ala Gln Arg Leu His
               170                 175                180
Leu Val Glu Gly Thr Ile Lys Thr Tyr Val Ser Ala Ile Phe Thr
               185                 190                195
Gln Leu Glu Val Arg Asn Arg Val Gln Ala Ala Ile Ile Ala Tyr
               200                 205                210
Glu Ala Gly Leu Val Lys Asp Ala Asp Leu Asn Arg
               215                 220
```

(2) INFORMATION FOR SEQ ID NO:3:

(i) SEQUENCE CHARACTERISTICS:
        (A) LENGTH: 103
        (B) TYPE: Amino Acid
        (C) STRANDEDNESS: Single
        (D) TOPOLOGY: Linear (ii) MOLECULE TYPE: Amino Acid (iii) HYPOTHETICAL: No (iv) ANTI-SENSE: No (v) FRAGMENT TYPE:

(vi) ORIGINAL SOURCE:
        (A) ORGANISM: Streptomyces coelicolor
        (B) STRAIN:
        (C) INDIVIDUAL ISOLATE:
        (D) DEVELOPMENTAL STAGE:
        (E) HAPLOTYPE:
        (F) TISSUE TYPE:

(G) CELL TYPE: unicellular microorganisms
                (H) CELL LINE:
                (I) ORGANELLE:

(vii) IMMEDIATE SOURCE:

(viii) POSITION IN GENOME:

(ix) FEATURE:
                (A) NAME/KEY: D7
                (B) LOCATION:
                (C) IDENTIFICATION METHOD: deduced
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (K) RELEVANT RESIDUES IN SEQ ID NO:

(xi) SEQUENCE DESCRIPTION: SEQ ID NO:3:

Ile Gly Asn Ser Arg Ala Leu Gly Leu Pro His His Arg Ala Ser
                    5                   10                      15

Arg Gly Pro His Gly Ala Arg Ala Asp Leu Leu Ala Gly Val Glu
                    20                  25                      30

Arg Leu Pro His Arg Leu Glu Glu Tyr Arg Lys Gly Gly Val Leu
                    35                  40                      45

Ala Arg Gly Ser Thr Pro Ala Asp Leu Gly Val Ile Met Arg Met
                    50                  55                      60

Thr Thr Ser Lys Gly Ala Gly Asn Pro Gly Leu Phe Gly Thr Val
                    65                  70                      75

Lys Gly Pro Asn Ile Glu Phe Ser Leu Asp Ser Val Ala Thr Lys
                    80                  85                      90

Asp Gly Tyr Arg Lys Thr Leu Arg Asp Leu Thr Ile Met
                    95                  100

(2) INFORMATION FOR SEQ ID NO:4:

(i) SEQUENCE CHARACTERISTICS:
                (A) LENGTH: 122
                (B) TYPE: Amino Acid
                (C) STRANDEDNESS: Single
                (D) TOPOLOGY: Linear (ii) MOLECULE TYPE: Amino Acid (iii) HYPOTHETICAL: No (iv) ANTI-SENSE: No (v) FRAGMENT TYPE:

(vi) ORIGINAL SOURCE:
                (A) ORGANISM: Streptomyces coelicolor
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE: unicellular microorganisms
                (H) CELL LINE:
                (I) ORGANELLE:

(vii) IMMEDIATE SOURCE:

(viii) POSITION IN GENOME:

(ix) FEATURE:

(A) NAME/KEY: D9
(B) LOCATION:
(C) IDENTIFICATION METHOD: deduced
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(K) RELEVANT RESIDUES IN SEQ ID NO:

(xi) SEQUENCE DESCRIPTION: SEQ ID NO:4:

| Val | Gly | Arg | Pro | Gly | Gln | Arg | Leu | Pro | Gly | Ala | Ala | Asp | Gly | Gly |
|---|---|---|---|---|---|---|---|---|---|---|---|---|---|---|
| | | | | 5 | | | | | 10 | | | | | 15 |
| Arg | Arg | Arg | Pro | Arg | His | His | Pro | Leu | Gln | Val | Leu | Pro | Pro | Asp |
| | | | | 20 | | | | | 25 | | | | | 30 |
| Ala | Pro | Arg | Gly | Arg | Arg | Gly | Pro | Pro | Leu | Pro | Ala | Asp | Pro | Asp |
| | | | | 35 | | | | | 40 | | | | | 45 |
| Leu | His | Arg | Arg | Val | Glu | Gly | Arg | Leu | Arg | Gly | Ala | Arg | Gly | Arg |
| | | | | 50 | | | | | 55 | | | | | 60 |
| Gly | Gly | Arg | Leu | Ala | Arg | Arg | Pro | Asp | Pro | Leu | Val | Arg | Arg | Gly |
| | | | | 65 | | | | | 70 | | | | | 75 |
| Pro | Arg | Glu | Val | Ala | Arg | Arg | Gly | Ile | Gly | Thr | Arg | Arg | Ala | Ala |
| | | | | 80 | | | | | 85 | | | | | 90 |
| Thr | Arg | Arg | Arg | Pro | His | Arg | Ala | Pro | Val | Ala | Asp | His | Val | Pro |
| | | | | 95 | | | | | 100 | | | | | 105 |
| Leu | Pro | Pro | Gly | Leu | Gly | Arg | Glu | Gly | Gly | Ala | Thr | Gly | Arg | Arg |
| | | | | 110 | | | | | 115 | | | | | 120 |
| Glu | Ala | | | | | | | | | | | | | |

(2) INFORMATION FOR SEQ ID NO:5:

(i) SEQUENCE CHARACTERISTICS:
(A) LENGTH: 446
(B) TYPE: Nucleotide
(C) STRANDEDNESS: Single
(D) TOPOLOGY: Linear (ii) MOLECULE TYPE: DNA (iii) HYPOTHETICAL: No (iv) ANTI-SENSE: No (v) FRAGMENT TYPE:

(vi) ORIGINAL SOURCE:
(A) ORGANISM: Streptomyces coelicolor
(B) STRAIN:
(C) INDIVIDUAL ISOLATE:
(D) DEVELOPMENTAL STAGE:
(E) HAPLOTYPE:
(F) TISSUE TYPE:
(G) CELL TYPE: unicellular microorganisms
(H) CELL LINE:
(I) ORGANELLE:

(vii) IMMEDIATE SOURCE:

(viii) POSITION IN GENOME:

(ix) FEATURE:
(A) NAME/KEY: Encodes D7
(B) LOCATION:
(C) IDENTIFICATION METHOD: sequencing
(D) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( K ) RELEVANT RESIDUES IN SEQ ID NO:

( x i ) SEQUENCE DESCRIPTION: SEQ ID NO:5:

| | | | | | |
|---|---|---|---|---|---|
| CCTAGGGCAA | CGACGCCCGG | TCGGGCTCGC | CCACCACGGC | CCGGCTTGCC | 50 |
| GGCCCCACCG | GGCGCGCCCG | CAGCTCGTCG | CGTGGCTGGA | GCGCGTTGCC | 100 |
| CACGGCGTCG | AGGAGCATTG | CGAACGGCGG | GTGGTCCCGG | GCGGGGCTCC | 150 |
| ACCCGCGCAG | GTCTGGCTGC | TAGTACGCGT | AGCAGCAGCT | GAAAGGGCGC | 200 |
| GGCAAGCCCG | GCTCCTTAGG | CCACTGGAAA | GGGCCTAACT | AGAGCTTGCT | 250 |
| CTCCAGGCTC | TGCCGGCAGA | ACAGCGGCAT | GGCGAACCAG | TCAGCCAGGT | 300 |
| TTCACTAGTA | GCGGACCACC | GAGGAAGGTT | TCAGTGCAGG | AGTTGCGATC | 350 |
| CCTCTCCGTC | CCCGTGCTTT | GTAGACCGCT | AGCCGTTGCT | GGCGTCAGCT | 400 |
| GAAAGCCGTC | TAGGCCGCCG | GCCCCGGCGA | GAACATCGCA | CGACCT | 446 |

( 2 ) INFORMATION FOR SEQ ID NO:6:

( i ) SEQUENCE CHARACTERISTICS:
        ( A ) LENGTH: 2588
        ( B ) TYPE: Nucleotide
        ( C ) STRANDEDNESS: Single
        ( D ) TOPOLOGY: Linear ( i i ) MOLECULE TYPE: DNA ( i i i ) HYPOTHETICAL: No ( i v ) ANTI-SENSE: No ( v ) FRAGMENT TYPE:

( v i ) ORIGINAL SOURCE:
        ( A ) ORGANISM: Streptomyces coelicolor
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE: unicellular microorganisms
        ( H ) CELL LINE:
        ( I ) ORGANELLE:

( v i i ) IMMEDIATE SOURCE:

( v i i i ) POSITION IN GENOME:

( i x ) FEATURE:
        ( A ) NAME/KEY: encodes AbsA1 and AbsA2
        ( B ) LOCATION:
        ( C ) IDENTIFICATION METHOD: sequencing
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( K ) RELEVANT RESIDUES IN SEQ ID NO:

( x i ) SEQUENCE DESCRIPTION: SEQ ID NO:6:

```
GCCTGGTGGC  TCCTTCCAAA  GTCACGTCCT  CAACGCTAGG  GAGAGGCAGG      50

GGCACGAAAC  ATCTGGCGAT  CGGCAACGAC  CGCAGTCGAC  TTTCGGCAGA     100

TCCGGCGGCC  GGGGCCGCTC  TTGTAGCGTG  CTGGAATGCA  CCGATGGCAG     150

GCCGTGCGCC  GACGAATCGA  ATCGCTTGTA  CGGGTCCTCG  GCTCCGAGCG     200

CCCGTTCACC  CGGCGCGCCG  ATCTGGTGCT  GCTGCTCGTA  CTGCTCGTGC     250

CCTCCGCGTT  CGCCACCGGG  ACGCTCGAGA  CCGCGCCGGT  CGCCTGGCTG     300

ACCGCGTGTC  TGCTCATCGC  GGCCGCGGTC  GTGGTGCAGC  GCACCGCGCC     350

GCTGCTGTCC  CTGCTGCTCG  CGGCGCTGCT  CACGCTGTTC  TATCCGTGGT     400

TCGGGGCGAA  CCTGTGGCCG  TCGATGGCGA  CGGTGGTGCT  GAGCTGCCTC     450

GCGGGCCGCA  GACTGACCCG  GCTGTGGCCC  GCGCACCTGG  TGTTCCTCTG     500

TGTCGCCGCG  GCCGGGCTCC  TGCTGGTGGC  CACCGTCGGC  CAGGGCAAGG     550

ACTGGCTGAG  CCTGCTGATG  ACCGAGTTCG  TCGCCTGTGT  GCTGCCCTGG     600

TGGCGGGCA   ACTGGTGGAG  CCAGCGCACC  GCGCTGACCC  ACGCCGGCTG     650

GGAGCACGCC  GAGCAACTGG  AGTGGCGCCA  GCGCTACATC  GCCGACCAGG     700

CCAGGATGAA  GGAGCGGGCC  AGGATCGCGC  AGGACATCAC  GACTCCCTGG     750

GCCACGAACT  GAGCGTGATG  GCCCTGCTCG  CCGGCGGCCT  GGAGCTGGCC     800

CCCGGGCTGT  CGGACCCGCA  CCGGGAGTCG  GTGGGCCAGT  TGCGGGAGCG     850

GTGCACGATG  GCCACCGAGC  GGCTGCACGA  GGTGATCGGG  CTGCTGCGGG     900

AGGACCCCAA  TCCGTCGCTG  ACCCCCGCCG  ACGAGTCCGT  CGCCCAGCTC     950

GTGCGCCGTT  TCCAGCGCTC  CGGTACGCCG  GTCCGGTTCC  AGGAGGACGG    1000

GGCCCGGGAC  CGCCCCGGCA  CGCCGCTGCT  GTCCGACCTC  GCGGCCTACC    1050

GGGTGGTGCA  GGAGGCGCTG  ACGAACGCGG  CCAAGCACGC  GCCGGGCGCG    1100

CCCATCGACG  TACGGGTGAC  GCACACCGCG  GACGAGACGG  TGGTGTCGGT    1150

CGTCAACGAG  CGGCCGGAGC  GGGGCGGGAG  TGTTCCGGCG  GCCGGGAGCG    1200

GGTCGGGGCT  GATCGGCCTC  GACGAGCGGG  TCCGGCTCGC  GGGCGGCACG    1250

CTGCGCACGG  GCCCGCGGGC  GGGCGGTTTC  GAGGTGTACG  CGCGACTGCC    1300

GCGCGGCGCC  TCCTCGCCGT  CGCGGTCCAC  CGAGCCGCCG  GGGCCGGCCG    1350

ACGGGGACGG  CACGGCCGGT  GGCTCGGGCG  ACGGCACGGC  GCCCGGGGCC    1400

GCGACGGCCG  GCAACGAGGG  GCGGGCCGCG  GCCGCCGCGG  CGGACCTGCC    1450

CGCCCCCTCC  GGGCCGTGGC  GCAGCGCCTC  CCGGGCCGCG  CTGCTGCGCA    1500

CCCGGGCCCG  GATCAGGCGG  GACGCCCGGC  GGGCCGCGCT  GATACCGGCG    1550

GTGCTCGGCG  CCGCCATCGT  GGCCTTCCTC  GGCGGGCTCT  ACGTCTTCAC    1600

CTCGGCGACC  ACGTCCCTCG  CCCCCGAGGA  CTACGCCCGG  ATCCGGGTGG    1650

GCGAGACCCG  CGCCGATCTG  GCCCCCGCGC  TGCCGGAGCG  CCGGATCAAG    1700

AAGCCGCCGC  CGGTCACCTC  CGAGCCGTCC  GTCCCGGCCG  GCACGACCTG    1750

CGAGTACTAC  CGGGCGAGCA  GCGGTCTGCT  CGACTTCGGC  GGCGCCATGT    1800

ACCGGCTGTG  CTTCAAGGAT  GATGTCCTCA  TGGCCAAGGA  CACGCTCTGA    1850

CCACCAGGGA  AGGATCGGAT  GATTCGCGTA  CTGCTCGCCG  ACGACGAGAC    1900

CATCATCAGG  GCCGGGGTTC  GCTCCATCCT  GACGACCGAA  CCGGGCATCG    1950

AGGTGGTCGC  CGAGGCGTCC  GACGGGCGGG  AGGCGGTGGA  ACTGGCCCGC    2000
```

```
AAGCACCGGC  CCGACGTGGC  CCTGCTCGAC  ATCCGGATGC  CGGAGATGGA              2050

CGGCCTGACG  GCCGCGGGTG  AGATGCGGAC  CACCAACCCG  GACACCGCGG              2100

TCGTCGTCCT  CACCACCTTC  GGGGAGGACC  GGTACATCGA  ACGGGCCCTG              2150

GACCAGGGCG  TGGCCGGGTT  CCTGCTCAAG  GCGTCCGATC  CGCGGGACCT              2200

GATCTCCGGC  GTACGGGCCG  TGGCGTCCGG  CGGCTCCTGC  CTCTCCCCGC              2250

TGGTGGCGCG  GCGGCTGATG  ACCGAGCTGC  GCCGGGCCCC  CTCACCGCGC              2300

TCGGAGGTGT  CGGGGGAGCG  CACGACGCTG  CTGACCAAGC  GGGAGCAGGA              2350

GGTCCTCGGC  ATGCTGGGGG  CCGGGCTGTC  GAACGCGGAG  ATCGCGCAGC              2400

GGCTGCACCT  GGTCGAGGGC  ACGATCAAGA  CGTATGTCAG  CGCCATCTTC              2450

ACCCAGTTGG  AGGTCCGCAA  CCGGGTGCAG  GCGGCGATCA  TCGCGTACGA              2500

GGCGGGACTG  GTGAAGGACG  CCGACCTCAA  CCGTTAGACG  CCGCGCGGTC              2550

CTTGACGAAG  CGGGCCAGCC  GCGTCGCCCC  CTCGGCGG                            2588
```

(2) INFORMATION FOR SEQ ID NO:7:

(i) SEQUENCE CHARACTERISTICS:
        (A) LENGTH: 371
        (B) TYPE: Nucleotide
        (C) STRANDEDNESS: Single
        (D) TOPOLOGY: Linear (ii) MOLECULE TYPE: DNA (iii) HYPOTHETICAL: No (iv) ANTI-SENSE: No (v) FRAGMENT TYPE:

(vi) ORIGINAL SOURCE:
        (A) ORGANISM: Streptomyces coelicolor
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE: unicellular microorganisms
        (H) CELL LINE:
        (I) ORGANELLE:

(vii) IMMEDIATE SOURCE:

(viii) POSITION IN GENOME:

(ix) FEATURE:
        (A) NAME/KEY: D9
        (B) LOCATION:
        (C) IDENTIFICATION METHOD: sequencing
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (K) RELEVANT RESIDUES IN SEQ ID NO:

(xi) SEQUENCE DESCRIPTION: SEQ ID NO:7:

```
AATCTGCGGC  GCGCCAGGAA  CTGCTTCGCC  CGGTCGGCGC  AGCGGGGGAG                50

CCGCCGCGCC  AGCCACCACT  CCATCGACGT  GCTCTCCGCC  TAGACGGCCA               100

GCGGGCGCAG  CAGGTCCACC  TTCACCGCGT  AGCCCCAGGT  CTACTGCGGC               150
```

-continued

| | | | | | |
|---|---|---|---|---|---|
| ATGAAGAGGC | GCCTCTGCAG | GTCGCGCCGG | AGCAGGCGGA | GCTTCCCGTG | 200 |
| CAGCTCCCAG | TCCTTCTTGG | GCGGCAGGCC | CAGCAAGGTG | GCGTGCGGCG | 250 |
| GGCTAAGGCC | ACGCGGCCCG | CCGTCAAGCC | GCCGCTCCCA | CAGCGCGTCC | 300 |
| GTGGCGTAGC | ACCTGACCAT | CACCGCCCGG | CTCCGGAGCA | AGCGGCGGGC | 350 |
| GTCAGGGGGC | GGCAAGACGT | C | | | 371 |